(12) United States Patent
Wei

(10) Patent No.: US 11,006,956 B2
(45) Date of Patent: *May 18, 2021

(54) GRASPING FOR TISSUE REPAIR

(71) Applicant: ABBOTT CARDIOVASCULAR SYSTEMS INC., Santa Clara, CA (US)

(72) Inventor: Michael F. Wei, Redwood City, CA (US)

(73) Assignee: ABBOTT CARDIOVASCULAR SYSTEMS INC., Santa Clara, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/813,566

(22) Filed: Mar. 9, 2020

(65) Prior Publication Data
US 2020/0205830 A1  Jul. 2, 2020

Related U.S. Application Data

(63) Continuation of application No. 16/748,450, filed on Jan. 21, 2020, which is a continuation of application
(Continued)

(51) Int. Cl.
*A61B 17/122* (2006.01)
*A61B 17/08* (2006.01)
(Continued)

(52) U.S. Cl.
CPC ............ *A61B 17/08* (2013.01); *A61B 17/122* (2013.01); *A61B 17/1285* (2013.01);
(Continued)

(58) Field of Classification Search
CPC ....... A61B 17/00; A61B 17/08; A61B 17/122; A61B 17/128; A61B 17/1285;
(Continued)

(56) References Cited

U.S. PATENT DOCUMENTS 2,097,018 A   10/1937  Chamberlain
2,108,206 A    2/1938  Meeker
(Continued)

FOREIGN PATENT DOCUMENTS

CA   2296317 C   1/2009
CN   1142351 A   2/1997
(Continued)

OTHER PUBLICATIONS

U.S. Appl. No. 14/216,787, filed Mar. 17, 2014, Basude, et al.
(Continued)

*Primary Examiner* — Vi X Nguyen
(74) *Attorney, Agent, or Firm* — Baker Botts L.L.P.

(57) ABSTRACT

The invention provides improved devices, systems, and methods for tissue approximation and repair at treatment sites. The invention provides devices, systems, and methods that may more successfully approximate and repair tissue by improving the capture of tissue into the devices. The invention may be a one-way mechanism that allows tissue to enter the mechanism but not easily exit, such as a leaf-spring, a protrusion, a pivoting arm and one or more frictional elements.

15 Claims, 8 Drawing Sheets

Related U.S. Application Data

No. 16/241,647, filed on Jan. 7, 2019, which is a continuation of application No. 14/577,852, filed on Dec. 19, 2014, now Pat. No. 10,188,392.

(51) Int. Cl.
  *A61B 17/128* (2006.01)
  *A61B 17/00* (2006.01)

(52) U.S. Cl.
  CPC ............... *A61B 2017/00243* (2013.01); *A61B 2017/00783* (2013.01); *A61B 2017/081* (2013.01)

(58) Field of Classification Search
  CPC .... A61B 17/32053; A61B 2017/00243; A61B 2017/00783; A61B 2017/081; A61B 17/0644; A61B 17/1122; A61F 2/0063
  See application file for complete search history.

(56) References Cited

U.S. PATENT DOCUMENTS

| | | |
|---|---|---|
| 3,296,668 A | 1/1967 | Aiken |
| 3,378,010 A | 4/1968 | Codling et al. |
| 3,557,780 A | 1/1971 | Sato |
| 3,671,979 A | 6/1972 | Moulopoulos |
| 3,675,639 A | 7/1972 | Cimber |
| 3,874,338 A | 4/1975 | Happel |
| 3,874,388 A | 4/1975 | King et al. |
| 4,007,743 A | 2/1977 | Blake |
| 4,055,861 A | 11/1977 | Carpentier et al. |
| 4,056,854 A | 11/1977 | Boretos et al. |
| 4,064,881 A | 12/1977 | Meredith |
| 4,091,815 A | 5/1978 | Larsen |
| 4,112,951 A | 9/1978 | Hulka et al. |
| 4,235,238 A | 11/1980 | Ogiu et al. |
| 4,297,749 A | 11/1981 | Davis et al. |
| 4,327,736 A | 5/1982 | Inoue |
| 4,340,091 A | 7/1982 | Skelton et al. |
| 4,458,682 A | 7/1984 | Cerwin |
| 4,425,908 A | 11/1984 | Simon |
| 4,484,579 A | 11/1984 | Meno et al. |
| 4,487,205 A | 12/1984 | Di Giovanni et al. |
| 4,498,476 A | 2/1985 | Cerwin et al. |
| 4,510,934 A | 4/1985 | Batra |
| 4,531,522 A | 7/1985 | Bedi et al. |
| 4,578,061 A | 3/1986 | Lemelson |
| 4,641,366 A | 2/1987 | Yokoyama et al. |
| 4,657,024 A | 4/1987 | Coneys |
| 4,686,965 A | 8/1987 | Bonnet et al. |
| 4,693,248 A | 9/1987 | Failla |
| 4,716,886 A | 1/1988 | Schulman et al. |
| 4,777,951 A | 10/1988 | Cribier et al. |
| 4,795,458 A | 1/1989 | Regan |
| 4,809,695 A | 3/1989 | Gwathmey et al. |
| 4,917,089 A | 4/1990 | Sideris |
| 4,930,674 A | 6/1990 | Barak |
| 4,944,295 A | 7/1990 | Gwathmey et al. |
| 4,969,890 A | 11/1990 | Sugita et al. |
| 4,994,077 A | 2/1991 | Dobben |
| 5,002,562 A | 3/1991 | Oberlander |
| 5,015,249 A | 5/1991 | Nakao et al. |
| 5,019,096 A | 5/1991 | Fox, Jr. et al. |
| 5,042,707 A | 8/1991 | Taheri |
| 5,047,041 A | 9/1991 | Samuels |
| 5,049,153 A | 9/1991 | Nakao et al. |
| 5,061,277 A | 10/1991 | Carpentier et al. |
| 5,069,679 A | 12/1991 | Taheri |
| 5,098,440 A | 3/1992 | Hillstead |
| 5,108,368 A | 4/1992 | Hammerslag et al. |
| 5,125,758 A | 6/1992 | DeWan |
| 5,125,895 A | 6/1992 | Buchbinder et al. |
| 5,147,370 A | 9/1992 | McNamara et al. |
| 5,171,252 A | 12/1992 | Friedland |
| 5,171,259 A | 12/1992 | Inoue |
| 5,190,554 A | 3/1993 | Coddington et al. |
| 5,195,968 A | 3/1993 | Lundquist et al. |
| 5,209,756 A | 5/1993 | Seedhom et al. |
| 5,222,963 A | 6/1993 | Brinkerhoff et al. |
| 5,226,429 A | 7/1993 | Kuzmak |
| 5,226,911 A | 7/1993 | Chee et al. |
| 5,234,437 A | 8/1993 | Sepetka |
| 5,242,456 A | 9/1993 | Nash et al. |
| 5,250,071 A | 10/1993 | Palermo |
| 5,251,611 A | 10/1993 | Zehel et al. |
| 5,254,130 A | 10/1993 | Poncet et al. |
| 5,261,916 A | 11/1993 | Engelson |
| 5,271,381 A | 12/1993 | Ailinger et al. |
| 5,271,544 A | 12/1993 | Fox et al. |
| 5,275,578 A | 1/1994 | Adams |
| 5,282,845 A | 2/1994 | Bush et al. |
| 5,304,131 A | 4/1994 | Paskar |
| 5,306,283 A | 4/1994 | Conners |
| 5,306,286 A | 4/1994 | Stack et al. |
| 5,312,415 A | 5/1994 | Palermo |
| 5,314,424 A | 5/1994 | Nicholas |
| 5,318,525 A | 6/1994 | West et al. |
| 5,320,632 A | 6/1994 | Heidmueller |
| 5,325,845 A | 7/1994 | Adair |
| 5,327,905 A | 7/1994 | Avitall |
| 5,330,442 A | 7/1994 | Green et al. |
| 5,330,501 A | 7/1994 | Tovey et al. |
| 5,332,402 A | 7/1994 | Teitelbaum |
| 5,334,217 A | 8/1994 | Das |
| 5,342,393 A | 8/1994 | Stack |
| 5,350,397 A | 9/1994 | Palermo et al. |
| 5,350,399 A | 9/1994 | Erlebacher et al. |
| 5,359,994 A | 11/1994 | Kreuter et al. |
| 5,363,861 A | 11/1994 | Edwards et al. |
| 5,368,564 A | 11/1994 | Savage |
| 5,368,601 A | 11/1994 | Sauer et al. |
| 5,383,886 A | 1/1995 | Kensey et al. |
| 5,389,077 A | 2/1995 | Melinyshyn et al. |
| 5,391,182 A | 2/1995 | Chin |
| 5,403,312 A | 4/1995 | Yates et al. |
| 5,403,326 A | 4/1995 | Harrison et al. |
| 5,411,552 A | 5/1995 | Andersen et al. |
| 5,417,699 A | 5/1995 | Klein et al. |
| 5,417,700 A | 5/1995 | Egan |
| 5,423,857 A | 6/1995 | Rosenman et al. |
| 5,423,858 A | 6/1995 | Bolanos et al. |
| 5,423,882 A | 6/1995 | Jackman et al. |
| 5,425,744 A | 6/1995 | Fagan et al. |
| 5,431,666 A | 7/1995 | Sauer et al. |
| 5,437,551 A | 8/1995 | Chalifoux |
| 5,437,681 A | 8/1995 | Meade et al. |
| 5,447,966 A | 9/1995 | Hermes et al. |
| 5,450,860 A | 9/1995 | O'Connor |
| 5,452,837 A | 9/1995 | Williamson, IV et al. |
| 5,456,400 A | 10/1995 | Shichman et al. |
| 5,456,674 A | 10/1995 | Bos et al. |
| 5,456,684 A | 10/1995 | Schmidt et al. |
| 5,462,527 A | 10/1995 | Stevens-Wright et al. |
| 5,472,044 A | 12/1995 | Hall et al. |
| 5,476,470 A | 12/1995 | Fitzgibbons, Jr. |
| 5,477,856 A | 12/1995 | Lundquist |
| 5,478,309 A | 12/1995 | Sweezer et al. |
| 5,478,353 A | 12/1995 | Yoon |
| 5,487,746 A | 1/1996 | Yu et al. |
| 5,496,332 A | 3/1996 | Sierra et al. |
| 5,507,725 A | 4/1996 | Savage et al. |
| 5,507,755 A | 4/1996 | Gresl et al. |
| 5,507,757 A | 4/1996 | Sauer et al. |
| 5,520,701 A | 5/1996 | Lerch |
| 5,522,873 A | 6/1996 | Jackman et al. |
| 5,527,313 A | 6/1996 | Scott et al. |
| 5,527,321 A | 6/1996 | Hinchliffe |
| 5,527,322 A | 6/1996 | Klein et al. |
| 5,536,251 A | 7/1996 | Evard et al. |
| 5,540,705 A | 7/1996 | Meade et al. |
| 5,542,949 A | 8/1996 | Yoon |
| 5,554,185 A | 9/1996 | Block et al. |
| 5,562,678 A | 10/1996 | Booker |

(56) References Cited

U.S. PATENT DOCUMENTS

| | | |
|---|---|---|
| 5,569,274 A | 10/1996 | Rapacki et al. |
| 5,571,085 A | 11/1996 | Accisano, III |
| 5,571,137 A | 11/1996 | Marlow et al. |
| 5,571,215 A | 11/1996 | Sterman et al. |
| 5,575,802 A | 11/1996 | McQuilkin et al. |
| 5,582,611 A | 12/1996 | Tsuruta et al. |
| 5,593,424 A | 1/1997 | Northrup, III |
| 5,593,435 A | 1/1997 | Carpentier et al. |
| 5,601,224 A | 2/1997 | Bishop et al. |
| 5,601,574 A | 2/1997 | Stefanchik et al. |
| 5,607,462 A | 3/1997 | Imran |
| 5,607,471 A | 3/1997 | Seguin et al. |
| 5,609,598 A | 3/1997 | Laufer et al. |
| 5,611,794 A | 3/1997 | Sauer et al. |
| 5,618,306 A | 4/1997 | Roth et al. |
| 5,620,452 A | 4/1997 | Yoon |
| 5,620,461 A | 4/1997 | Muijs Van De Moer et al. |
| 5,626,588 A | 5/1997 | Sauer et al. |
| 5,634,932 A | 6/1997 | Schmidt |
| 5,636,634 A | 6/1997 | Kordis et al. |
| 5,639,277 A | 6/1997 | Mariant et al. |
| 5,640,955 A | 6/1997 | Ockuly et al. |
| 5,649,937 A | 7/1997 | Bito et al. |
| 5,662,681 A | 9/1997 | Nash et al. |
| 5,669,917 A | 9/1997 | Sauer et al. |
| 5,690,671 A | 11/1997 | McGurk et al. |
| 5,695,504 A | 12/1997 | Gifford, III et al. |
| 5,695,505 A | 12/1997 | Yoon |
| 5,702,825 A | 12/1997 | Keita et al. |
| 5,706,824 A | 1/1998 | Whittier |
| 5,709,707 A | 1/1998 | Lock et al. |
| 5,713,910 A | 2/1998 | Gordon et al. |
| 5,713,911 A | 2/1998 | Racene et al. |
| 5,715,817 A | 2/1998 | Stevens-Wright et al. |
| 5,716,367 A | 2/1998 | Koike et al. |
| 5,716,417 A | 2/1998 | Girard et al. |
| 5,718,725 A | 2/1998 | Sterman et al. |
| 5,719,725 A | 2/1998 | Nakao |
| 5,722,421 A | 3/1998 | Francese et al. |
| 5,725,542 A | 3/1998 | Yoon |
| 5,725,556 A | 3/1998 | Moser et al. |
| 5,738,649 A | 4/1998 | Macoviak |
| 5,741,280 A | 4/1998 | Fleenor |
| 5,741,297 A | 4/1998 | Simon |
| 5,749,828 A | 5/1998 | Solomon et al. |
| 5,755,778 A | 5/1998 | Kleshinski |
| 5,759,193 A | 6/1998 | Burbank et al. |
| 5,769,812 A | 6/1998 | Stevens et al. |
| 5,769,863 A | 6/1998 | Garrison |
| 5,772,578 A | 6/1998 | Heimberger et al. |
| 5,782,239 A | 7/1998 | Webster, Jr. |
| 5,782,845 A | 7/1998 | Shewchuk |
| 5,797,927 A | 8/1998 | Yoon |
| 5,797,960 A | 8/1998 | Stevens et al. |
| 5,810,847 A | 9/1998 | Laufer et al. |
| 5,810,849 A | 9/1998 | Kontos |
| 5,810,853 A | 9/1998 | Yoon |
| 5,810,876 A | 9/1998 | Kelleher |
| 5,814,029 A | 9/1998 | Hassett |
| 5,814,097 A | 9/1998 | Sterman et al. |
| 5,820,592 A | 10/1998 | Hammerslag |
| 5,820,631 A | 10/1998 | Nobles |
| 5,823,955 A | 10/1998 | Kuck et al. |
| 5,823,956 A | 10/1998 | Roth et al. |
| 5,824,065 A | 10/1998 | Gross |
| 5,827,237 A | 10/1998 | Macoviak et al. |
| 5,829,447 A | 11/1998 | Stevens et al. |
| 5,833,671 A | 11/1998 | Macoviak et al. |
| 5,836,955 A | 11/1998 | Buelna et al. |
| 5,840,081 A | 11/1998 | Andersen et al. |
| 5,843,031 A | 12/1998 | Hermann et al. |
| 5,843,178 A | 12/1998 | Vanney et al. |
| 5,849,019 A | 12/1998 | Yoon |
| 5,853,422 A | 12/1998 | Huebsch et al. |
| 5,855,271 A | 1/1999 | Eubanks et al. |
| 5,855,590 A | 1/1999 | Malecki et al. |
| 5,855,601 A | 1/1999 | Bessler et al. |
| 5,855,614 A | 1/1999 | Stevens et al. |
| 5,860,990 A | 1/1999 | Nobles et al. |
| 5,861,003 A | 1/1999 | Latson et al. |
| 5,868,733 A | 2/1999 | Ockuly et al. |
| 5,876,399 A | 3/1999 | Chia et al. |
| 5,879,307 A | 3/1999 | Chio et al. |
| 5,885,271 A | 3/1999 | Hamilton et al. |
| 5,891,160 A | 4/1999 | Williamson, IV et al. |
| 5,916,147 A | 6/1999 | Boury |
| 5,928,224 A | 7/1999 | Laufer |
| 5,944,733 A | 8/1999 | Engelson |
| 5,947,363 A | 9/1999 | Bolduc et al. |
| 5,954,732 A | 9/1999 | Hart et al. |
| 5,957,949 A | 9/1999 | Leonhard et al. |
| 5,972,020 A | 10/1999 | Carpentier et al. |
| 5,972,030 A | 10/1999 | Garrison et al. |
| 5,976,159 A | 11/1999 | Bolduc et al. |
| 5,980,455 A | 11/1999 | Daniel et al. |
| 5,989,284 A | 11/1999 | Laufer |
| 6,015,417 A | 1/2000 | Reynolds, Jr. |
| 6,017,358 A | 1/2000 | Yoon et al. |
| 6,019,722 A | 2/2000 | Spence et al. |
| 6,022,360 A | 2/2000 | Reimels et al. |
| 6,033,378 A | 3/2000 | Lundquist et al. |
| 6,036,699 A | 3/2000 | Andreas et al. |
| 6,048,351 A | 4/2000 | Gordon et al. |
| 6,056,769 A | 5/2000 | Epstein et al. |
| 6,059,757 A | 5/2000 | Macoviak et al. |
| 6,060,628 A | 5/2000 | Aoyama et al. |
| 6,060,629 A | 5/2000 | Pham et al. |
| 6,063,106 A | 5/2000 | Gibson |
| 6,066,146 A | 5/2000 | Carroll et al. |
| 6,068,628 A | 5/2000 | Fanton et al. |
| 6,068,629 A | 5/2000 | Haissaguerre et al. |
| 6,077,214 A | 6/2000 | Mortier et al. |
| 6,079,414 A | 6/2000 | Roth |
| 6,086,600 A | 7/2000 | Kortenbach |
| 6,088,889 A | 7/2000 | Luther et al. |
| 6,099,505 A | 8/2000 | Ryan et al. |
| 6,099,553 A | 8/2000 | Hart et al. |
| 6,110,145 A | 8/2000 | Macoviak |
| 6,117,144 A | 9/2000 | Nobles et al. |
| 6,117,159 A | 9/2000 | Huebsch et al. |
| 6,120,496 A | 9/2000 | Whayne et al. |
| 6,123,699 A | 9/2000 | Webster, Jr. |
| 6,126,658 A | 10/2000 | Baker |
| 6,132,447 A | 10/2000 | Dorsey |
| 6,136,010 A | 10/2000 | Modesitt et al. |
| 6,143,024 A | 11/2000 | Campbell et al. |
| 6,149,658 A | 11/2000 | Gardiner et al. |
| 6,159,240 A | 12/2000 | Sparer et al. |
| 6,162,233 A | 12/2000 | Williamson, IV et al. |
| 6,165,164 A | 12/2000 | Hill et al. |
| 6,165,183 A | 12/2000 | Kuehn et al. |
| 6,165,204 A | 12/2000 | Levinson et al. |
| 6,168,614 B1 | 1/2001 | Andersen et al. |
| 6,171,320 B1 | 1/2001 | Monassevitch |
| 6,182,664 B1 | 2/2001 | Cosgrove |
| 6,187,003 B1 | 2/2001 | Buysse et al. |
| 6,190,408 B1 | 2/2001 | Melvin |
| 6,193,734 B1 | 2/2001 | Bolduc et al. |
| 6,200,315 B1 | 3/2001 | Gaiser et al. |
| 6,203,531 B1 | 3/2001 | Ockuly et al. |
| 6,203,553 B1 | 3/2001 | Robertson et al. |
| 6,206,893 B1 | 3/2001 | Klein et al. |
| 6,206,907 B1 | 3/2001 | Marino et al. |
| 6,210,419 B1 | 4/2001 | Mayenberger et al. |
| 6,210,432 B1 | 4/2001 | Solem et al. |
| 6,217,528 B1 | 4/2001 | Koblish et al. |
| 6,245,079 B1 | 6/2001 | Nobles et al. |
| 6,267,746 B1 | 7/2001 | Bumbalough |
| 6,267,781 B1 | 7/2001 | Tu |
| 6,269,819 B1 | 8/2001 | Oz et al. |
| 6,277,555 B1 | 8/2001 | Duran et al. |
| 6,283,127 B1 | 9/2001 | Sterman et al. |
| 6,283,962 B1 | 9/2001 | Tu et al. |
| 6,290,674 B1 | 9/2001 | Roue et al. |

(56) References Cited

U.S. PATENT DOCUMENTS

| | | |
|---|---|---|
| 6,299,637 B1 | 10/2001 | Shaolian et al. |
| 6,306,133 B1 | 10/2001 | Tu et al. |
| 6,312,447 B1 | 11/2001 | Grimes |
| 6,319,250 B1 | 11/2001 | Falwell et al. |
| 6,322,559 B1 | 11/2001 | Daulton et al. |
| 6,332,880 B1 | 12/2001 | Yang et al. |
| 6,332,893 B1 | 12/2001 | Mortier et al. |
| 6,346,074 B1 | 2/2002 | Roth |
| 6,352,708 B1 | 3/2002 | Duran et al. |
| 6,355,030 B1 | 3/2002 | Aldrich et al. |
| 6,358,277 B1 | 3/2002 | Duran |
| 6,368,326 B1 | 4/2002 | Dakin et al. |
| 6,387,104 B1 | 5/2002 | Pugsley, Jr. et al. |
| 6,402,780 B2 | 6/2002 | Williamson et al. |
| 6,402,781 B1 | 6/2002 | Langberg et al. |
| 6,406,420 B1 | 6/2002 | McCarthy et al. |
| 6,419,669 B1 | 7/2002 | Frazier et al. |
| 6,419,696 B1 | 7/2002 | Ortiz et al. |
| 6,461,366 B1 | 10/2002 | Seguin |
| 6,464,707 B1 | 10/2002 | Bjerken |
| 6,482,224 B1 | 11/2002 | Michler et al. |
| 6,485,489 B2 | 11/2002 | Teirstein et al. |
| 6,508,828 B1 | 1/2003 | Akerfeldt et al. |
| 6,533,796 B1 | 3/2003 | Sauer et al. |
| 6,537,314 B2 | 3/2003 | Langberg et al. |
| 6,540,755 B2 | 4/2003 | Ockuly et al. |
| 6,544,215 B1 | 4/2003 | Bencini et al. |
| 6,551,303 B1 | 4/2003 | Van Tassel et al. |
| 6,551,331 B2 | 4/2003 | Nobles et al. |
| 6,562,037 B2 | 5/2003 | Paton et al. |
| 6,562,052 B2 | 5/2003 | Nobles et al. |
| 6,575,971 B2 | 6/2003 | Hauck et al. |
| 6,585,761 B2 | 7/2003 | Taheri |
| 6,599,311 B1 | 7/2003 | Biggs et al. |
| 6,616,684 B1 | 9/2003 | Vidlund et al. |
| 6,619,291 B2 | 9/2003 | Hlavka et al. |
| 6,626,899 B2 | 9/2003 | Houser et al. |
| 6,626,930 B1 | 9/2003 | Allen et al. |
| 6,629,534 B1 | 10/2003 | St. Goar et al. |
| 6,641,592 B1 | 11/2003 | Sauer et al. |
| 6,656,221 B2 | 12/2003 | Taylor et al. |
| 6,669,687 B1 | 12/2003 | Saadat |
| 6,685,648 B2 | 2/2004 | Flaherty et al. |
| 6,689,164 B1 | 2/2004 | Seguin |
| 6,695,866 B1 | 2/2004 | Kuehn et al. |
| 6,701,929 B2 | 3/2004 | Hussein |
| 6,702,825 B2 | 3/2004 | Frazier et al. |
| 6,702,826 B2 | 3/2004 | Liddicoat et al. |
| 6,709,382 B1 | 3/2004 | Homer |
| 6,709,456 B2 | 3/2004 | Langberg et al. |
| 6,718,985 B2 | 4/2004 | Hlavka et al. |
| 6,719,767 B1 | 4/2004 | Kimblad |
| 6,723,038 B1 | 4/2004 | Schroeder et al. |
| 6,726,716 B2 | 4/2004 | Marquez |
| 6,740,107 B2 | 5/2004 | Loeb et al. |
| 6,746,471 B2 | 6/2004 | Mortier et al. |
| 6,752,813 B2 | 6/2004 | Goldfarb et al. |
| 6,755,777 B2 | 6/2004 | Schweich et al. |
| 6,764,510 B2 | 7/2004 | Vidlund et al. |
| 6,767,349 B2 | 7/2004 | Ouchi |
| 6,770,083 B2 | 8/2004 | Seguin |
| 6,797,001 B2 | 9/2004 | Mathis et al. |
| 6,797,002 B2 | 9/2004 | Spence et al. |
| 6,837,867 B2 | 1/2005 | Kortelling |
| 6,855,137 B2 | 2/2005 | Bon |
| 6,860,179 B2 | 3/2005 | Hopper et al. |
| 6,875,224 B2 | 4/2005 | Grimes |
| 6,908,481 B2 | 6/2005 | Cribier |
| 6,926,715 B1 | 8/2005 | Hauck et al. |
| 6,926,730 B1 | 8/2005 | Nguyen et al. |
| 6,945,978 B1 | 9/2005 | Hyde |
| 6,949,122 B2 | 9/2005 | Adams et al. |
| 6,966,914 B2 | 11/2005 | Abe |
| 6,986,775 B2 | 1/2006 | Morales et al. |
| 7,004,970 B2 | 2/2006 | Cauthen, III et al. |
| 7,011,669 B2 | 3/2006 | Kimblad |
| 7,048,754 B2 | 5/2006 | Martin et al. |
| 7,101,395 B2 | 9/2006 | Tremulis et al. |
| 7,112,207 B2 | 9/2006 | Allen et al. |
| 7,226,467 B2 | 6/2007 | Lucatero et al. |
| 7,288,097 B2 | 10/2007 | Seguin |
| 7,381,210 B2 | 6/2008 | Zarbatany et al. |
| 7,464,712 B2 | 12/2008 | Oz et al. |
| 7,497,822 B1 | 3/2009 | Kugler et al. |
| 7,533,790 B1 | 5/2009 | Knodel et al. |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,604,646 B2 | 10/2009 | Goldfarb et al. |
| 7,635,329 B2 | 12/2009 | Goldfarb et al. |
| 7,651,502 B2 | 1/2010 | Jackson |
| 7,655,015 B2 | 2/2010 | Goldfarb et al. |
| 7,798,953 B1 | 9/2010 | Wilk |
| 7,972,323 B1 | 7/2011 | Bencini et al. |
| 8,062,313 B2 | 11/2011 | Kimblad |
| 8,118,822 B2 | 2/2012 | Schaller et al. |
| 8,500,761 B2 * | 8/2013 | Goldfarb ............ A61B 17/0487 606/151 |
| 10,188,392 B2 * | 1/2019 | Wei ....................... A61B 17/122 |
| 2001/0004715 A1 | 6/2001 | Duran et al. |
| 2001/0005787 A1 | 6/2001 | Oz et al. |
| 2001/0010005 A1 | 7/2001 | Kammerer et al. |
| 2001/0018611 A1 | 8/2001 | Solem et al. |
| 2001/0022872 A1 | 9/2001 | Marui |
| 2001/0037084 A1 | 11/2001 | Nardeo |
| 2001/0039411 A1 | 11/2001 | Johansson et al. |
| 2001/0044568 A1 | 11/2001 | Langberg et al. |
| 2002/0013571 A1 | 1/2002 | Goldfarb et al. |
| 2002/0022848 A1 | 2/2002 | Garrison et al. |
| 2002/0026233 A1 | 2/2002 | Shaknovich |
| 2002/0035361 A1 | 3/2002 | Houser et al. |
| 2002/0035381 A1 | 3/2002 | Bardy et al. |
| 2002/0042651 A1 | 4/2002 | Liddicoat et al. |
| 2002/0055767 A1 | 5/2002 | Forde et al. |
| 2002/0055774 A1 | 5/2002 | Liddicoat |
| 2002/0055775 A1 | 5/2002 | Carpentier et al. |
| 2002/0058910 A1 | 5/2002 | Hermann et al. |
| 2002/0058995 A1 | 5/2002 | Stevens |
| 2002/0077687 A1 | 6/2002 | Ahn |
| 2002/0087148 A1 | 7/2002 | Brock et al. |
| 2002/0087169 A1 | 7/2002 | Brock et al. |
| 2002/0087173 A1 | 7/2002 | Alferness et al. |
| 2002/0103532 A1 | 8/2002 | Langberg et al. |
| 2002/0107534 A1 | 8/2002 | Schaefer et al. |
| 2002/0147456 A1 | 10/2002 | Diduch et al. |
| 2002/0156526 A1 | 10/2002 | Hilavka et al. |
| 2002/0158528 A1 | 10/2002 | Tsuzaki et al. |
| 2002/0161378 A1 | 10/2002 | Downing |
| 2002/0169360 A1 | 11/2002 | Taylor et al. |
| 2002/0183766 A1 | 12/2002 | Seguin |
| 2002/0183787 A1 | 12/2002 | Wahr et al. |
| 2002/0183835 A1 | 12/2002 | Taylor et al. |
| 2003/0005797 A1 | 1/2003 | Hopper et al. |
| 2003/0045778 A1 | 3/2003 | Ohline et al. |
| 2003/0050693 A1 | 3/2003 | Quijano et al. |
| 2003/0069570 A1 | 4/2003 | Witzel et al. |
| 2003/0069593 A1 | 4/2003 | Tremulis et al. |
| 2003/0069636 A1 | 4/2003 | Solem et al. |
| 2003/0074012 A1 | 4/2003 | Nguyen et al. |
| 2003/0078654 A1 | 4/2003 | Taylor et al. |
| 2003/0083742 A1 | 5/2003 | Spence et al. |
| 2003/0105519 A1 | 6/2003 | Fasol et al. |
| 2003/0105520 A1 | 6/2003 | Alferness et al. |
| 2003/0120340 A1 | 6/2003 | Lisk et al. |
| 2003/0120341 A1 | 6/2003 | Shennib et al. |
| 2003/0130669 A1 | 7/2003 | Damarati |
| 2003/0130730 A1 | 7/2003 | Cohn et al. |
| 2003/0144697 A1 | 7/2003 | Mathis et al. |
| 2003/0167071 A1 | 9/2003 | Martin et al. |
| 2003/0171776 A1 | 9/2003 | Adams et al. |
| 2003/0187467 A1 | 10/2003 | Schreck |
| 2003/0195562 A1 | 10/2003 | Collier et al. |
| 2003/0208231 A1 | 11/2003 | Williamson, IV et al. |
| 2003/0229395 A1 | 12/2003 | Cox |

(56) References Cited

U.S. PATENT DOCUMENTS

| | | |
|---|---|---|
| 2003/0233038 A1 | 12/2003 | Hassett |
| 2004/0002719 A1 | 1/2004 | Oz et al. |
| 2004/0003819 A1 | 1/2004 | St. Goar et al. |
| 2004/0019377 A1 | 1/2004 | Taylor et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0034365 A1 | 2/2004 | Lentz et al. |
| 2004/0039442 A1 | 2/2004 | St. Goar et al. |
| 2004/0039443 A1 | 2/2004 | Solem et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0049211 A1 | 3/2004 | Tremulis et al. |
| 2004/0073302 A1 | 4/2004 | Rourke et al. |
| 2004/0078053 A1 | 4/2004 | Berg et al. |
| 2004/0087975 A1 | 5/2004 | Lucatero et al. |
| 2004/0088047 A1 | 5/2004 | Spence et al. |
| 2004/0092962 A1 | 5/2004 | Thorton et al. |
| 2004/0097878 A1 | 5/2004 | Anderson et al. |
| 2004/0097979 A1 | 5/2004 | Svanidze et al. |
| 2004/0106989 A1 | 6/2004 | Wilson et al. |
| 2004/0111099 A1 | 6/2004 | Nguyen et al. |
| 2004/0122448 A1 | 6/2004 | Levine |
| 2004/0127981 A1 | 7/2004 | Randert et al. |
| 2004/0127982 A1 | 7/2004 | Machold et al. |
| 2004/0127983 A1 | 7/2004 | Mortier et al. |
| 2004/0133062 A1 | 7/2004 | Pai et al. |
| 2004/0133063 A1 | 7/2004 | McCarthy et al. |
| 2004/0133082 A1 | 7/2004 | Abraham-Fuchs et al. |
| 2004/0133192 A1 | 7/2004 | Houser et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0138745 A1 | 7/2004 | Macoviak et al. |
| 2004/0148021 A1 | 7/2004 | Cartledge et al. |
| 2004/0152847 A1 | 8/2004 | Emri et al. |
| 2004/0152947 A1 | 8/2004 | Schroeder et al. |
| 2004/0153144 A1 | 8/2004 | Seguin |
| 2004/0158123 A1 | 8/2004 | Jayaraman |
| 2004/0162610 A1 | 8/2004 | Laiska et al. |
| 2004/0167539 A1 | 8/2004 | Kuehn et al. |
| 2004/0186486 A1 | 9/2004 | Roue et al. |
| 2004/0186566 A1 | 9/2004 | Hindrichs et al. |
| 2004/0193191 A1 | 9/2004 | Starksen et al. |
| 2004/0215339 A1 | 10/2004 | Drasler et al. |
| 2004/0220593 A1 | 11/2004 | Greenhalgh |
| 2004/0220657 A1 | 11/2004 | Nieminen et al. |
| 2004/0225300 A1 | 11/2004 | Goldfarb et al. |
| 2004/0236354 A1 | 11/2004 | Seguin |
| 2004/0243229 A1 | 12/2004 | Vidlund et al. |
| 2004/0249452 A1 | 12/2004 | Adams et al. |
| 2004/0249453 A1 | 12/2004 | Cartledge et al. |
| 2004/0260393 A1 | 12/2004 | Randert et al. |
| 2005/0004583 A1 | 1/2005 | Oz et al. |
| 2005/0004665 A1 | 1/2005 | Aklog |
| 2005/0004668 A1 | 1/2005 | Aklog et al. |
| 2005/0021056 A1 | 1/2005 | St. Goer et al. |
| 2005/0021057 A1 | 1/2005 | St. Goer et al. |
| 2005/0021058 A1 | 1/2005 | Negro |
| 2005/0033446 A1 | 2/2005 | Deem et al. |
| 2005/0038508 A1 | 2/2005 | Gabbay |
| 2005/0049698 A1 | 3/2005 | Bolling et al. |
| 2005/0055089 A1 | 3/2005 | Macoviak et al. |
| 2005/0059351 A1 | 3/2005 | Cauwels et al. |
| 2005/0149014 A1 | 7/2005 | Hauck et al. |
| 2005/0159810 A1 | 7/2005 | Filsoufi |
| 2005/0197694 A1 | 9/2005 | Pai et al. |
| 2005/0197695 A1 | 9/2005 | Stacchino et al. |
| 2005/0216039 A1 | 9/2005 | Lederman |
| 2005/0228422 A1 | 10/2005 | Machold et al. |
| 2005/0228495 A1 | 10/2005 | Macoviak |
| 2005/0251001 A1 | 11/2005 | Hassett |
| 2005/0267493 A1 | 12/2005 | Schreck et al. |
| 2005/0273160 A1 | 12/2005 | Lashinski et al. |
| 2005/0287493 A1 | 12/2005 | Novak et al. |
| 2006/0004247 A1 | 1/2006 | Kute et al. |
| 2006/0015003 A1 | 1/2006 | Moaddes et al. |
| 2006/0020275 A1 | 1/2006 | Goldfarb et al. |
| 2006/0030866 A1 | 2/2006 | Schreck |
| 2006/0030867 A1 | 2/2006 | Zadno |
| 2006/0030885 A1 | 2/2006 | Hyde |
| 2006/0058871 A1 | 3/2006 | Zakay et al. |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0089671 A1 | 4/2006 | Goldfarb et al. |
| 2006/0089711 A1 | 4/2006 | Dolan |
| 2006/0135993 A1 | 6/2006 | Seguin |
| 2006/0184203 A1 | 8/2006 | Martin et al. |
| 2006/0195012 A1 | 8/2006 | Mortier et al. |
| 2006/0229708 A1 | 10/2006 | Powell et al. |
| 2006/0252984 A1 | 11/2006 | Randert et al. |
| 2007/0038293 A1 | 2/2007 | St. Goar et al. |
| 2007/0100356 A1 | 5/2007 | Lucatero et al. |
| 2007/0118155 A1 | 5/2007 | Goldfarb et al. |
| 2007/0129737 A1 | 6/2007 | Goldfarb et al. |
| 2007/0197858 A1* | 8/2007 | Goldfarb ............... A61F 2/246 600/37 |
| 2007/0198082 A1 | 8/2007 | Kapadia et al. |
| 2008/0039935 A1 | 2/2008 | Buch et al. |
| 2008/0051703 A1 | 2/2008 | Thorton et al. |
| 2008/0051807 A1 | 2/2008 | St. Goar et al. |
| 2008/0097489 A1 | 4/2008 | Goldfarb et al. |
| 2008/0167714 A1 | 7/2008 | St. Goer et al. |
| 2008/0183194 A1 | 7/2008 | Goldfarb et al. |
| 2009/0156995 A1 | 6/2009 | Martin et al. |
| 2009/0163934 A1 | 6/2009 | Raschdorf, Jr. et al. |
| 2009/0177266 A1 | 7/2009 | Powell et al. |
| 2009/0198322 A1 | 8/2009 | Deem et al. |
| 2009/0270858 A1 | 10/2009 | Hauck et al. |
| 2009/0326567 A1 | 12/2009 | Goldfarb et al. |
| 2010/0016958 A1 | 1/2010 | St. Goer et al. |
| 2010/0022823 A1 | 1/2010 | Goldfarb et al. |
| 2010/0324585 A1 | 12/2010 | Miles et al. |
| 2013/0066342 A1 | 3/2013 | Dell et al. |
| 2014/0249553 A1 | 9/2014 | Kimura et al. |

FOREIGN PATENT DOCUMENTS

| | | |
|---|---|---|
| DE | 3504292 C1 | 7/1986 |
| DE | 101 16 168 A1 | 11/2001 |
| EP | 0 179 562 B1 | 7/1989 |
| EP | 0 558 031 B1 | 2/1993 |
| EP | 0 558 031 A2 | 9/1993 |
| EP | 0 684 012 A2 | 11/1995 |
| EP | 0 727 239 A2 | 8/1996 |
| EP | 0 782 836 A1 | 7/1997 |
| EP | 1 230 899 A1 | 8/2002 |
| EP | 1383448 A2 | 1/2004 |
| EP | 1 674 040 A2 | 6/2006 |
| FR | 2 768 324 A1 | 3/1999 |
| FR | 2768324 A1 | 3/1999 |
| GB | 1 598 111 A | 9/1981 |
| GB | 2 151 142 A | 7/1985 |
| JP | 09-253030 A | 9/1997 |
| JP | 11-089937 A | 4/1999 |
| JP | 2000-283130 A | 10/2000 |
| JP | 2015-502548 A | 1/2015 |
| WO | WO 81/00668 A1 | 3/1981 |
| WO | WO 91/01689 A1 | 2/1991 |
| WO | WO 91/18881 A1 | 12/1991 |
| WO | WO 92/12690 A1 | 8/1992 |
| WO | WO 94/18881 A1 | 9/1994 |
| WO | WO 94/18893 A1 | 9/1994 |
| WO | WO 95/11620 A2 | 5/1995 |
| WO | WO 95/15715 A1 | 6/1995 |
| WO | WO 96/14032 A1 | 5/1996 |
| WO | WO 96/20655 A1 | 7/1996 |
| WO | WO 96/22735 A1 | 8/1996 |
| WO | WO 96/30072 A1 | 10/1996 |
| WO | WO 96/32882 A1 | 10/1996 |
| WO | WO 97/18746 A2 | 5/1997 |

(56) References Cited

FOREIGN PATENT DOCUMENTS

| | | |
|---|---|---|
| WO | WO 97/25927 A1 | 7/1997 |
| WO | WO 97/26034 A1 | 7/1997 |
| WO | WO 97/27807 A1 | 8/1997 |
| WO | WO 97/38748 A2 | 10/1997 |
| WO | WO 97/39688 A2 | 10/1997 |
| WO | WO 97/48436 A2 | 12/1997 |
| WO | WO 98/07375 A1 | 2/1998 |
| WO | WO 98/24372 A1 | 6/1998 |
| WO | WO 98/30153 A1 | 7/1998 |
| WO | WO 98/32382 A1 | 7/1998 |
| WO | WO 98/35638 A1 | 8/1998 |
| WO | WO 99/00059 A1 | 1/1999 |
| WO | WO 99/01377 A1 | 1/1999 |
| WO | WO 99/07354 A2 | 2/1999 |
| WO | WO 99/13777 A1 | 3/1999 |
| WO | WO 99/15223 A1 | 4/1999 |
| WO | WO 99/66967 A1 | 12/1999 |
| WO | WO 00/02489 A1 | 1/2000 |
| WO | WO 00/03651 A1 | 1/2000 |
| WO | WO 00/03759 A2 | 1/2000 |
| WO | WO 00/12168 A1 | 3/2000 |
| WO | WO 00/44313 A1 | 8/2000 |
| WO | WO 00/59382 A1 | 10/2000 |
| WO | WO 00/60995 A2 | 10/2000 |
| WO | WO 01/00111 A1 | 1/2001 |
| WO | WO 01/00114 A1 | 1/2001 |
| WO | WO 01/03651 A2 | 1/2001 |
| WO | WO 01/26557 A1 | 4/2001 |
| WO | WO 01/26586 A1 | 4/2001 |
| WO | WO 01/26587 A1 | 4/2001 |
| WO | WO 01/26588 A2 | 4/2001 |
| WO | WO 01/26703 A1 | 4/2001 |
| WO | WO 01/28432 A1 | 4/2001 |
| WO | WO 01/28455 A1 | 4/2001 |
| WO | WO 01/47438 A1 | 7/2001 |
| WO | WO 01/49213 A2 | 7/2001 |
| WO | WO 01/50985 A1 | 7/2001 |
| WO | WO 01/54618 A1 | 8/2001 |
| WO | WO 01/56512 A1 | 8/2001 |
| WO | WO 01/66001 A2 | 9/2001 |
| WO | WO 01/70320 A1 | 9/2001 |
| WO | WO 01/89440 A2 | 11/2001 |
| WO | WO 01/95831 A2 | 12/2001 |
| WO | WO 01/95832 A2 | 12/2001 |
| WO | WO 01/97741 A2 | 12/2001 |
| WO | WO 02/00099 A2 | 1/2002 |
| WO | WO 02/01999 A2 | 1/2002 |
| WO | WO 02/03892 A1 | 1/2002 |
| WO | WO 02/34167 A2 | 5/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 03/001893 A2 | 1/2003 |
| WO | WO 03/003930 A1 | 1/2003 |
| WO | WO 03/020179 A1 | 3/2003 |
| WO | WO 03/028558 A2 | 4/2003 |
| WO | WO 03/037171 A2 | 5/2003 |
| WO | WO 03/047467 A1 | 6/2003 |
| WO | WO 03/049619 A2 | 6/2003 |
| WO | WO 03/073910 A2 | 9/2003 |
| WO | WO 03/073913 A2 | 9/2003 |
| WO | WO 03/082129 A2 | 10/2003 |
| WO | WO 03/105667 A2 | 12/2003 |
| WO | WO 2004/004607 A1 | 1/2004 |
| WO | WO 2004/012583 A2 | 2/2004 |
| WO | WO 2004/012789 A2 | 2/2004 |
| WO | WO 2004/014282 A2 | 2/2004 |
| WO | WO 2004/019811 A2 | 3/2004 |
| WO | WO 2004/030570 A2 | 4/2004 |
| WO | WO 2004/037317 A2 | 5/2004 |
| WO | WO 2004/045370 A2 | 6/2004 |
| WO | WO 2004/045378 A2 | 6/2004 |
| WO | WO 2004/045463 A2 | 6/2004 |
| WO | WO 2004/047679 A1 | 6/2004 |
| WO | WO 2004/062725 A1 | 7/2004 |
| WO | WO 2004/082523 A2 | 9/2004 |
| WO | WO 2004/082538 A2 | 9/2004 |
| WO | WO 2004/093730 A2 | 11/2004 |
| WO | WO 04/103162 A2 | 12/2004 |
| WO | WO 2004/103162 A2 | 12/2004 |
| WO | WO 2004/112585 A2 | 12/2004 |
| WO | WO 2004/112651 A2 | 12/2004 |
| WO | WO 2005/002424 A2 | 1/2005 |
| WO | WO 2005/018507 A2 | 3/2005 |
| WO | WO 2005/027797 A1 | 3/2005 |
| WO | WO 2005/032421 A2 | 4/2005 |
| WO | WO 2005/062931 A2 | 7/2005 |
| WO | WO 2005/112792 A2 | 12/2005 |
| WO | WO 2006/037073 A2 | 4/2006 |
| WO | WO 2006/105008 A1 | 10/2006 |
| WO | WO 2006/105009 A1 | 10/2006 |
| WO | WO 2006/115875 A2 | 11/2006 |
| WO | WO 2006/115876 A2 | 11/2006 |
| WO | WO 2010/128502 A1 | 11/2010 |

OTHER PUBLICATIONS

U.S. Appl. No. 14/577,852 (U.S. Pat. No. 10,188,392), filed Dec. 19, 2014 (Jan. 29, 2019).
U.S. Appl. No. 16/241,647 (US 2019/0133581), filed Jan. 7, 2019 (May 9, 2019).
U.S. Appl. No. 16/748,450, filed Jan. 21, 2020.
U.S. Appl. No. 14/577,852, Dec. 13, 2018 Issue Fee Payment.
U.S. Appl. No. 14/577,852, Sep. 28, 2018 Notice of Allowance.
U.S. Appl. No. 14/577,852, Sep. 14, 2018 Notice of Allowance.
U.S. Appl. No. 14/577,852, Jul. 25, 2018 Request for Continued Examination (RCE).
U.S. Appl. No. 14/577,852, May 15, 2018 Notice of Allowance.
U.S. Appl. No. 14/577,852, Apr. 25, 2018 Notice of Allowance.
U.S. Appl. No. 14/577,852, Mar. 6, 2018 Response to Non-Final Office Action.
U.S. Appl. No. 14/577,852, Sep. 7, 2017 Non-Final Office Action.
U.S. Appl. No. 14/577,852, Aug. 16, 2017 Amendment and Request for Continued Examination (RCE).
U.S. Appl. No. 14/577,852, May 16, 2017 Final Office Action.
U.S. Appl. No. 14/577,852, Jan. 20, 2017 Response to Non-Final Office Action.
U.S. Appl. No. 14/577,852, Oct. 20, 2016 Non-Final Office Action.
U.S. Appl. No. 14/577,852, Sep. 14, 2016 Response to Restriction Requirement.
U.S. Appl. No. 14/577,852, Jul. 14, 2016 Restriction Requirement.
U.S. Appl. No. 16/748,450, Apr. 6, 2020 Response to Restriction Requirement.
U.S. Appl. No. 16/748,450, Mar. 27, 2020 Restriction Requirement.
Abe et al., De Vega's Annuloplasty for Acquired Tricuspid Disease: Early and Late Results in 110 Patients, Ann. Thorac. Surg., Jan. 1989, pp. 670-676, vol. 48.
Abe et al., "De Vega's Annuloplasty for Acquired Tricuspid Disease: Early and Late Results in 110 Patients," Ann. Thorac. Surg. 62:1876-1877 (1996).
Agricola et al., "Mitral Valve Reserve in Double Orifice Technique: an Exercise Echocardiographic Study," Journal of Heart Valve Disease, 11(5):637-643 (2002).
Alfieri et al., "An Effective Technique to Correct Anterior Mitral Leaflet Prolapse," J. Card Surg., 14:468-470 (1999).
Alfieri et al., "Novel Suture Device for Beating Heart Mitral Leaflet Approximation," Annals of Thoracic Surgery, 74:1488-1493 (2002).
Alfieri et al., "The double orifice technique in mitral valve repair: a simple solution for complex problems," Journal of Thoracic and Cardiovascular Surgery, 122:674-681 (2001).
Alfieri et al., "The Edge to Edge Technique," The European Association for Cardio-Thoracic Surgery, 14th Annual Meeting, Frankfurt / Germany, Oct. 7-11, 2000, Post Graduate Courses, Book of Proceedings.
Alfieri, "The Edge-to-Edge Repair of the Mitral Valve," [Abstract] 6th Annual New Era Cardiac Care: Innovation & Technology, Heart Surgery Forum, (Jan. 2003) pp. 103.

(56) References Cited

OTHER PUBLICATIONS

Alt Khan et al, Blade Atrial Septostomy: Experience with the First 50 Procedures, Cathet. Cardiovasc. Diagn., Aug. 1991, pp. 257-262, vol. 23.
Alvarez et al., Repairing the Degenerative Mitral Valve: Ten to Fifteen-year Follow-up, J. Thorac. Cardiovasc. Surg., Aug. 1996, pp. 238-247, vol. 112.
Arisi et al., "Mitral Valve Repair with Alfieri Technique in Mitral Regurgitation of Diverse Etiology: Early Echocardiographic Results," Circulation Supplement II, 104(17):3240 (2001).
Bach et al., Early Improvement in Congestive Heart Failure After Correction of Secondary Mitral Regurgitation in End-stage Cardiomyopathy, Am. Heart J., Jun. 1995, pp. 1165-1170, vol. 129.
Bach et al., Improvement Following Correction of Secondary Mitral Regurgitation in End-stage Cardiomyopathy with Mitral Annuloplasty, Am. J. Cardiol., Oct. 15, 1996, pp. 966-969, vol. 78.
Bailey, "Mitral Regurgitation" in Surgery of the Heart, Chapter 20, pp. 686-737 (1955).
Bernal et al., "The Valve Racket: a new and different concept of atrioventricular valve repair," Eur. J. Cardio-thoracic Surgery 29:1026-1029 (2006).
Bhudia et al., "Edge-to-Edge (Alfieri) Mitral Repair: Results in Diverse Clinical Settings," Ann Thorac Surg, 77:1598-1606 (2004).
Bhudia et al., "Edge-to-edge Mitral Repair: A Versatile Mitral Repair," http://www.sts.org/doc/7007 accessed on Sep. 24, 2008.
Bhudia, #58 Edge-to-edge mitral repair: a versatile mitral repair technique, 2003 STS Presentation, [Abstract Only], 2004.
Bolling et al., Surgery for Acquired Heart Disease: Early Outcome of Mitral Valve Reconstruction in Patients with End-stage Cardiomyopathy, J. Thor. and Cardiovasc. Surg., Apr. 1995, pp. 676-683, vol. 109.
Borghetti et al., "Preliminary observations on haemodynamics during physiological stress conditions following 'double-orifice' mitral valve repair," European Journal of Cardio-thoracic Surgery, 20:262-269 (2001).
Castedo, "Edge-to-Edge Tricuspid Repair for Redeveloped Valve Incompetence after DeVega's Annuloplasty," Ann Thora Surg., 75:605-606 (2003).
Chinese Office Action dated Sep. 9, 2013 in Application No. 200980158707.2 (with English translation).
Communication dated Apr. 16, 2018 from the European Patent Office in counterpart European application No. 04752603.3.
Communication dated Apr. 28, 2017 issued by the European Patent Office in counterpart application No. 16196023.2.
Communication dated Jan. 26, 2017, from the European Patent Office in counterpart European application No. 16196023.2.
Communication dated May 8, 2017, from the European Patent Office in counterpart European Application No. 04752714.8.
Dec et al., Idiopathic Dilated Cardiomyopathy, N. Engl. J. Med., Dec. 8, 1994, pp. 1564-1575, vol. 331.
Derwent citing German language patent, EP 684012 published Nov. 12, 1995, for: "Thread for constructing surgical seam—has flexible section with two ends, with lower fastening part on thread first end having hollow cylinder with continuous hole through which surgical needle threads".
Derwent citing Japanese language patent, JP 11089937 published Jun. 4, 1999, for: "Catheter for mitral regurgitation test—includes jet nozzles provided on rear side of large diametered spindle shaped portion attached to end of narrow diametered tube".
Dottori et al., "Echocardiographic imaging of the Alfieri type mitral valve repair," Ital. Heart J., 2(4):319-320 (2001).
Downing et al., "Beating heart mitral valve surgery: Preliminary model and methodology," Journal of Thoracic and Cardiovascular Surgery, 123(6):1141-1146 (2002).
Extended European Search Report, dated Oct. 17, 2014, issued in European Patent Application No. 06751584.1.
Falk et al., "Computer-Enhanced Mitral Valve Surgery: Toward a Total Endoscopic Procedure," Seminars in Thoracic and Cardiovascular Surgery, 11(3):244-249 (1999).

Filsoufi et al., "Restoring Optimal Surface of Coaptation With a Mini Leaflet Prosthesis: A New Surgical Concept for the Correction of Mitral Valve Prolapse," Intl. Soc. for Minimally Invasive Cardiothoracic Surgery 1(4):186-87 (2006).
Frazier et al., "Early Clinical Experience with an Implantable, Intracardiac Circulatory Support Device: Operative Considerations and Physiologic Implications," http://www.sts.org/doc/7007 accessed on Sep. 24, 2008.
Fucci et al., Improved Results with Mitral Valve Repair Using New Surgical Techniques, Eur. J. Cardiothorac. Surg., Nov. 1995, pp. 621-627, vol. 9.
Fundaro et al., "Chordal Plication and Free Edge Remodeling for Mitral Anterior Leaflet Prolapse Repair: 8-Year Follow-up," Annals of Thoracic Surgery, 72:1515-1519 (2001).
Garcia-Rinaldi et al., "Left Ventricular Volume Reduction and Reconstruction is Ischemic Cardiomyopathy," Journal of Cardiac Surgery, 14:199-210 (1999).
Gateliene et al., "Early and late postoperative results of mitral and tricuspid valve insufficiency surgical treatment using edge-to-edge central coaptation procedure," Medicina (Kaunas) 38(Suppl. 2):172-175 (2002).
Gatti et al., "The edge to edge technique as a trick to rescue an imperfect mitral valve repair," Eur. J. Cardiothorac Surg, 22:817-820 (2002).
Gillinov et al., "Is Minimally Invasive Heart Valve Surgery a Paradigm for the Future?" Current Cardiology Reports, 1:318-322 (1999).
Gundry et al., "Facile Mitral Valve Repair Utilizing Leaflet Edge Approximation: Midterm Results of the Alfieri Figure of Eight Repair," The Western Thoracic Surgical Association, Scientific Session (May 1999).
Gupta et al., "Influence of Older Donor Grafts on Heart Transplant Survival: Lack of Recipient Effects," http://www.sts.org/doc/7007 accessed on Sep. 24, 2008.
Ikeda et al., "Batista's Operation with Coronary Artery Bypass Grafting and Mitral Valve Plasty for Ischemic Dilated Cardiomyopathy," The Japanese Journal of Thoracic and Cardiovascular Surgery, 48:746-749 (2000).
International Search Report and Written Opinion of PCT Application No. PCT/US2009/068023, dated Mar. 2, 2010, 10 pages total.
Izzat et al., "Early Experience with Partial Left Ventriculectomy in the Asia-Pacific Region," Annals of Thoracic Surgery, 67:1703-1707 (1999).
Kallner et al., "Transaortic Approach for the Alfieri Stitch," Ann Thorac Surg, 71:378-380 (2001).
Kameda et al., Annuloplasty for Severe Mitral Regurgitation Due to Dilated Cardiomyopathy, Ann. Thorac. Surg., 1996, pp. 1829-1832, vol. 61.
Kavarana et al., "Transaortic Repair of Mitral Regurgitation," The Heart Surgery Forum, #2000-2389, 3(1):24-28 (2000).
Kaza et al., "Ventricular Reconstruction Results in Improved Left Ventricular Function and Amelioration of Mitral Insufficiency," Annals of Surgery, 235(6):828-832 (2002).
Kherani et al., "The Edge-To-Edge Mitral Valve Repair: The Columbia Presbyterian Experience," Ann. Thorac. Surg., 78:73-76 (2004).
Konertz et al., "Results After Partial Left Ventriculectomy in a European Heart Failure Population," Journal of Cardiac Surgery, 14:129-135 (1999).
Kron et al., "Surgical Relocation of the Posterior Papillary Muscle in Chronic Ischemic Mitral Regurgitation," Annals. of Thoracic Surgery, 74:600-601 (2002).
Kruger et al., "P73—Edge to Edge Technique in Complex Mitral Valve Repair," Thorac Cardiovasc Surg., 48(Suppl. 1):106 (2000).
Langer et al., "Posterier mitral leaflet extensions: An adjunctive repair option for ischemic mitral regurgitation?" J Thorac Cardiovasc Surg, 131:868-877 (2006).
Lorusso et al., "'Double-Orifice' Technique to Repair Extensive Mitral Valve Excision Following Acute Endocarditis," J. Card Surg, 13:24-26 (1998).
Lorusso et al., "The double-orifice technique for mitral valve reconstruction: predictors of postoperative outcome," Eur J. Cardiothorac Surg, 20:583-589 (2001).

(56) References Cited

OTHER PUBLICATIONS

Maisano et al., The Edge-to-edge Technique: A Simplified Method to Correct Mitral Insufficiency, Eur. J. Cardiothorac. Surg., Jan. 14, 1998, pp. 240-246, vol. 13.
Maisano et al., "The Double Orifice Repair for Barlow Disease: A Simple Solution for Complex Repair," Circulation 100(18):I94 (1999).
Maisano et al., "The double orifice technique as a standardized approach to treat mitral regurgitation due to severe myxomatous disease: surgical technique," European Journal of Cardio-thoracic Surgery, 17:201-205 (2000).
Maisano et al., "The hemodynamic effects of double-orifice valve repair for mitral regurgitation: a 3D computational model," European Journal of Cardio-thoracic Surgery, 15:419-425 (1999).
Maisano et al., "Valve repair for traumatic tricuspid regurgitation," Eur. J. Cardio-thorac Surg, 10:867-873 (1996).
Mantovani et al., "Edge-to-edge Repair of Congenital Familiar Tricuspid Regurgitation: Case Report," J. Heart Valve Dis., 9:641-643 (2000).
McCarthy et al., Tricuspid Valve Repair with the Cosgrove-Edwards Annuloplasty System, Ann. Thorac. Surg., Jan. 16, 1997, pp. 267-268, vol. 64.
McCarthy et al., "Partial left ventriculectomy and mitral valve repair for end-stage congestive heart failure," European Journal of Cardio-thoracic Surgery, 13:337-343 (1998).
Moainie et al., "Correction of Traumatic Tricuspid Regurgitation Using the Double Orifice Technique," Annals of Thoracic Surgery, 73:963-965 (2002).
Morales et al., "Development of an Off Bypass Mitral Valve Repair," The Heart Surgery Forum #1999-4693, 2(2):115-120 (1999).
Nakanishi et al., "Early Outcome with the Alfieri Mitral Valve Repair," J. Cardiol., 37:263-266 (2001) [Abstract in English; Article in Japanese].
Nielsen et al., "Edge-to-Edge Mitral Repair: Tension of the Approximating Suture and Leaflet Deformation During Acute Ischemic Mitral Regurgitation in the Ovine Heart," Circulation, 104(Suppl. I):I-29-I-35 (2001).
Noera et al., "Tricuspid Valve Incompetence Caused by Nonpenetrating Thoracic Trauma", Annals of Thoracic Surgery, 51:320-322 (1991).
Osawa et al., "Partial Left Ventriculectomy in a 3-Year Old Boy with Dilated Cardiomyopathy," Japanese Journal of Thoracic and Cardiovascular Surg, 48:590-593 (2000).
Park et al., Clinical Use of Blade Atrial Septostomy, Circulation, 1978, pp. 600-608, vol. 58.
Patel et al., "Epicardial Atrial Defibrillation: Novel Treatment of Postoperative Atrial Fibrillation," http://www.sts.org/doc/7007 accessed on Sep. 23, 2008.
Privitera et al., "Alfieri Mitral Valve Repair: Clinical Outcome and Pathology," Circulation, 106:e173-e174 (2002).
Redaelli et al., "A Computational Study of the Hemodynamics After 'Edge-To-Edge' Mitral Valve Repair," Journal of Biomechanical Engineering, 123:565-570 (2001).
Reul et al., "Mitral Valve Reconstruction for Mitral Insufficiency," Progress in Cardiovascular Diseases, XXXIX(6):567-599 (1997).
Ricchi et al., Linear Segmental Annuloplasty for Mitral Valve Repair, Ann. Thorac. Surg., Jan. 7, 1997, pp. 1805-1806, vol. 63.
Robicsek et al., "The Bicuspid Aortic Valve. How Does It Function? Why Does It Fail," http://www.sts.org/doc/7007 accessed on Sep. 24, 2008.
Supplemental European Search Report of EP Application No. 02746781, dated May 13, 2008, 3 pages total.
Supplementary European Search Report issued in European Application No. 05753261.6 dated Jun. 9, 2011, 3 pages total.
Tager et al., Long-Term Follow-Up of Rheumatic Patients Undergoing Left-Sided Valve Replacement with Tricuspid Annuloplasty—Validity of Preoperative Echocardiographic Criteria in the Decision to Perform Tricuspid Annuloplasty, Am. J. Cardiol., Apr. 15, 1998, pp. 1013-1016, vol. 81.

Tamura et al., "Edge to Edge Repair for Mitral Regurgitation in a Patient with Chronic Hemodialysis: Report of a Case," Kyobu Geka. The Japanese Journal of Thoracic Surgery, 54(9):788-790 (2001).
Tibayan et al., "Annular Geometric Remodeling in Chronic Ischemic Mitral Regurgitation," http://www.sts.org/doc/7007 accessed on Sep. 24, 2008.
Timek et al., "Edge-to-edge mitral repair: gradients and three-dimensional annular dynamics in vivo during inotropic stimulation," Eur J. of Cardiothoracic Surg., 19:431-437 (2001).
Timek, "Edge-to-Edge Mitral Valve Repair without Annuloplasty Ring in Acute Ischemic Mitral Regurgitation," [Abstract] Clinical Science, Abstracts from Scientific Sessions, 106(19):2281 (2002).
Totaro, "Mitral valve repair for isolated prolapse of the anterior leaflet: an 11-year follow-up," European Journal of Cardio-thoracic Surgery, 15:119-126 (1999).
Uchida et al, Percutaneous Cardiomyotomy and Valvulotomy with Angioscopic Guidance, Am. Heart J., Apr. 1991, pp. 1221-1224, vol. 121.
Umana et al, 'Bow-Tie' Mitral Valve Repair: An Adjuvant Technique for Ischemic Mitral Regurgitation, Ann. Thorac. Surg., May 12, 1998, pp. 1640-1646, vol. 66.
Umana et al., "'Bow-tie' Mitral Valve Repair Successfully Addresses Subvalvular Dysfunction in Ischemic Mitral Regurgitation," Surgical Forum, XLVIII:279-280 (1997).
Votta et al., "3-D Computational Analysis of the Stress Distribution on the Leaflets after Edge-to-Edge Repair of Mitral Regurgitation," Journal of Heart Valve Disease, 11:810-822 (2002).
U.S. Appl. No. 60/128,690, filed Apr. 9, 1999, Deem, et al.
Arthur C. Beall et al., Clinical Experience with a Dacron Velour-Covered Teflon-Disc Mitral Valve Prosthesis, 5 Ann. Thorac. Surg. 402-10 (1968).
C. Fucci et al., Improved Results with Mitral Valve Repair Using New Surgical Techniques, 9 Eur. J. Cardiothorac. Surg. 621-27 (1995).
F. Maisano et al., The Edge-to-Edge Technique: A Simplified Method to Correct Mitral Insufficiency, 13 J. Cardio-thoracic Surgery 240-46 (1998).
Gregg W. Stone et al., Clinical Trial Design Principles and Endpoint Definitions for Transcatheter Mitral Valve Repair and Replacement: Part 1: Clinical Trial Design Principles: A Consensus Document from the Mitral Valve Academic Research Consortium, 66 J. Am. Coll. Cardiol. 278-307 (2015).
Juan P. Umaña et al., "Bow-Tie" Mitral Valve Repair: An Adjuvant Technique for Ischemic Mitral Regurgitation, 66 Annals of Thoracic Surgery 1640-46 (1998).
Netter, F. H., et al., "The Ciba Collection of Medical Illustrations," vol. 5. Royal Victorian Institute for the Blind Tertiary Resource Service, Melbourne (1969).
Randas J. V. Batista et al., Partial Left Ventriculectomy to Treat End-Stage Heart Disease, 64 Ann. Thorac. Surg. 634-38 (1997).
Ross M. Reul et al., Mitral Valve Reconstruction for Mitral Insufficiency, 39 Progress in Cardiovascular Diseases 567-99 (1997).
U.S. Appl. No. 60/051,078, filed Jun. 27, 1997, Oz, et al.
Alfieri, O., et al., "Novel Suture Device for Beating-Heart Mitral Leaflet Approximation," Ann Thorac Surg 74:1488-93 (2002).
Alfieri, O., et al., "The Double-orifice Technique in Mitral Valve Repair: A Simple Solution for Complex Problems," Journal of Thoracic and Cardiovascular Surgery 122(4):674-681 (2001).
Cribier, A., et al., "Percutaneous Mitral Valvotomy with a Metal Dilatator," The Lancet 349:1667 (1997).
Feldman, T., et al., "Technique of Percutaneous Transvenous Mitral Commissurotomy Using the Inoue Balloon Catheter," Catheterization and Cardiovascular Diagnosis Supplement 2:26-34 (1994).
Glazier, J. and Turi, Z., "Percutaneous Balloon Mitral Valvuloplasty," Progress in Cardiovascular Diseases 40(1):5-26 (1997).
Hung et al., "Atrial Septal Puncture Technique in Percutaneous Transvenous Mitral Commissurotomy : Mitral Valvuloplasty Using the Inoue Balloon Catheter Technique," Catheterization and Cardiovascular Diagnosis 26: 275-284 (1992).
Hung et al., "Pitfalls and Tips in Inoue Balloon Mitral Commissurotomy," Catheterization and Cardiovascular Diagnosis, 37:188-199 (1996).

(56) References Cited

OTHER PUBLICATIONS

Inoue, K. and Feldman, T., "Percutaneous Transvenous Mitral Commissurotomy Using the Inoue Balloon Catheter," Catheterization and Cardiovascular Diagnosis 28:119-125 (1993).
Inoue, K., et al., "Clinical Application of Transvenous Mitral Commissurotomy by a New Balloon Catheter," J Thorac Cardiovasc Surg 87:394-402 (1984).
Lau, K. and Hung, J., "'Balloon Impasse'; A Marker for Severe Mitral Subvalvular Disease and a Predictor of Mitral Regurgitation in Inoue-Balloon Percutaneous Transvenous Mitral Commissurotomy," Catheterization and Cardiovascular Diagnosis 35:310-319 (1995).
Lock et al., "Transcatheter Closure of Atrial Septal Defects: Experimental Studies," Circulation 79:1091-1099 (1989).
McCarthy, P., et al., "Early Results with Partial Left Ventriculectomy," J Thorac Cardiovasc Surg 114(5):755-765 (1997).
Morales et al., "Development of an Off Bypass Mitral Valve Repair," The Heart Surgery Forum, 2(2):115-120 (1999).
O'Rourke, R. and Crawford, M., "Mitral Valve Regurgitation," Year Book Medical Publishers, Inc. 1-52 (1984).
Otto, Catherine M., "Timing of Surgery in Mitral Regurgitation," Heart 89:100-105 (2003).
Werker, P. and Kon M., "Review of Facilitated Approaches to Vascular Anastomosis Surgery," Ann Thorac Surg 63:122-7 (1997).
Extended European Search Report dated Jan. 13, 2020 in Application No. EP 19209511.
Copelan, "How Dr. Oz Kick-Started a Groundbreaking Device for Patients with Heart Failure," Parade (Sep. 26, 2018).
Cribier et al., "Percutaneous Mechanical Mitral Commissurotomy With a Newly Designed Metallic Valvulotome: Immediate Results of the Initial Experience in 153 Patients," Circulation 99:793-799 (1999).
Dias de Azeredo Bastos et al., "Percutaneous Mechanical Mitral Commissurotomy Performed With a Cribier's Metallic Valvulotome. Initial Results," Arq Bras Cardiol, 77:126-131 (2001).
Freeny et al., "Subselective Diagnostic and Interventional Arteriography Using a Simple Coaxial Catheter System," Cardiovasc. Intervent. Radiol. 7:209-213 (1984).
Ing et al., "The Snare-Assisted Technique for Transcatheter Coil Occlusion of Moderate to Large Patent Ductus Arteriosus: Immediate and Intermediate Results," J. Am. Col. Cardiol. 33(6):1710-1718 (1999).
Rahhal, "Tiny device to 'zip up' leaky hearts invented by Dr Oz 20 years ago could save millions, study finds," Daily Mail (Sep. 26, 2018).
U.S. Appl. No. 60/316,892 to Tremulis et al., filed Aug. 31, 2001.
Waller et al., "Anatomic Basis for and Morphologic Results from Catheter Balloon Valvuloplasty of Stenotic Mitral Valves," Clin. Cardiol. 13:655-661 (1990).

\* cited by examiner

GRASPING FOR TISSUE REPAIR

CROSS REFERENCE TO RELATED APPLICATIONS

The present application is a continuation application of U.S. patent application Ser. No. 16/748,450, filed on Jan. 21, 2020, which is a continuation application of U.S. patent application Ser. No. 16/241,647, filed on Jan. 7, 2019, which is a continuation application of U.S. patent application Ser. No. 14/577,852, filed on Dec. 19, 2014, issued as U.S. Pat. No. 10,188,392, the entire contents of which are incorporated herein by reference.

BACKGROUND

The present invention relates generally to medical methods, devices, and systems. In particular, the present invention relates to methods, devices, and systems for the endovascular, percutaneous, or minimally invasive surgical treatment of bodily tissues, such as tissue approximation or valve repair. More particularly, the present invention relates to repairing heart valves and venous valves, and devices and methods for removing or disabling mitral valve repair components through minimally invasive procedures.

Surgical repair of bodily tissues often involves tissue approximation and fastening of such tissues in the approximated arrangement. When repairing valves, tissue approximation includes coapting the leaflets of the valves in a therapeutic arrangement which may then be maintained by fastening or fixing the leaflets. Such coaptation can be used to treat regurgitation which most commonly occurs in the mitral valve.

Mitral valve regurgitation is characterized by retrograde flow from the left ventricle of a heart through an incompetent mitral valve into the left atrium. During a normal cycle of heart contraction (systole), the mitral valve acts as a check valve to prevent oxygenated blood from flowing back into the left atrium. In this way, oxygenated blood is pumped into the aorta through the aortic valve. Mitral valve regurgitation can significantly decrease the pumping efficiency of the heart, placing the patient at risk of severe, progressive heart failure.

Mitral valve regurgitation can result from a number of different mechanical defects in the mitral valve or the left ventricular wall. The valve leaflets, the valve chordae which connect the leaflets to the papillary muscles, the papillary muscles themselves, or the left ventricular wall may be damaged or otherwise dysfunctional. Commonly, the valve annulus may be damaged, dilated, or weakened, limiting the ability of the mitral valve to close adequately against the high pressures of the left ventricle.

The most common treatments for mitral valve regurgitation rely on valve replacement or repair including leaflet and annulus remodeling, the latter generally referred to as valve annuloplasty. One technique for mitral valve repair which relies on suturing adjacent segments of the opposed valve leaflets together is referred to as the "bow-tie" or "edge-to-edge" technique. While all these techniques can be effective, they usually rely on open heart surgery where the patient's chest is opened, typically via a sternotomy, and the patient placed on cardiopulmonary bypass. The need to both open the chest and place the patient on bypass is traumatic and has associated high mortality and morbidity.

In some patients, a fixation device can be installed into the heart using minimally invasive techniques. The fixation device can hold the adjacent segments of the opposed valve leaflets together and may reduce mitral valve regurgitation. One such device used to clip the anterior and posterior leaflets of the mitral valve together is the MitraClip® fixation device, sold by Abbott Vascular, Santa Clara, Calif., USA.

DESCRIPTION OF THE BACKGROUND ART

Many techniques exist for approximating and repairing tissues and organs at treatment sites. For example, minimally invasive and percutaneous techniques for coapting and modifying mitral valve leaflets to treat mitral valve regurgitation are described in PCT Publication Nos. WO 98/35638; WO 99/00059; WO 99/01377; and WO 00/03759; WO 2000/060995; WO 2004/103162. Maisano et al. (1998) Eur. J. Cardiothorac. Surg. 13:240-246; Fucci et al. (1995) Eur. J. Cardiothorac. Surg. 9:621-627; and Umana et al. (1998) Ann. Thorac. Surg. 66:1640-1646, describe open surgical procedures for performing "edge-to-edge" or "bow-tie" mitral valve repair where edges of the opposed valve leaflets are sutured together to lessen regurgitation. Dec and Fuster (1994) N. Engl. J. Med. 331:1564-1575 and Alvarez et al. (1996) J. Thorac. Cardiovasc. Surg. 112:238-247 are review articles discussing the nature of and treatments for dilated cardiomyopathy.

Mitral valve annuloplasty is described in the following publications: Bach and Bolling (1996) Am. J. Cardiol. 78:966-969; Kameda et al. (1996) Ann. Thorac. Surg. 61:1829-1832; Bach and Bolling (1995) Am. Heart J. 129: 1165-1170; and Bolling et al. (1995) 109:676-683. Linear segmental annuloplasty for mitral valve repair is described in Ricchi et al. (1997) Ann. Thorac. Surg. 63:1805-1806. Tricuspid valve annuloplasty is described in McCarthy and Cosgrove (1997) Ann. Thorac. Surg. 64:267-268; Tager et al. (1998) Am. J. Cardiol. 81:1013-1016; and Abe et al. (1989) Ann. Thorac. Surg. 48:670-676.

Percutaneous transluminal cardiac repair procedures are described in Park et al. (1978) Circulation 58:600-608; Uchida et al. (1991) Am. Heart J. 121: 1221-1224; and Ali Khan et al. (1991) Cathet. Cardiovasc. Diagn. 23:257-262. Endovascular cardiac valve replacement is described in U.S. Pat. Nos. 5,840,081; 5,411,552; 5,554,185; 5,332,402; 4,994,077; and 4,056,854. U.S. Pat. No. 3,671,979 describes a catheter for temporary placement of an artificial heart valve.

Other percutaneous and endovascular cardiac repair procedures are described in U.S. Pat. Nos. 4,917,089; 4,484, 579; and 3,874,338; and PCT Publication No. WO 91/01689.

Thoracoscopic and other minimally invasive heart valve repair and replacement procedures are described in U.S. Pat. Nos. 5,855,614; 5,829,447; 5,823,956; 5,797,960; 5,769, 812; and 5,718,725.

BRIEF SUMMARY

The present disclosure describes devices intended for intravascular delivery and for use in treating mitral valve defects in human patients. The mitral valve of a human heart has an atrial side, a ventricular side, an anterior leaflet, a posterior leaflet, and an opening between the leaflets.

In one embodiment, the device can include a body, a pair of proximal elements, and a pair of distal elements. Each proximal element is coupled at a first end to the body on opposite sides of the body, and has a free second end. Each proximal element has a proximal engagement surface between its first and second ends. Each proximal engagement surface is configured to approximate and engage a portion of the leaflets adjacent the mitral valve on the atrial side. Each proximal engagement surface also has a proximal retaining element configured to permit tissue to move toward the first end of the proximal element and to resist movement of the tissue away from the first end of the proximal element.

Each distal element is pivotally coupled at a first end to the body on opposite sides of the body, and has a free second end. Each distal element has a distal engagement surface between its first and second ends. Each distal engagement surface is configured to approximate and engage a portion of the leaflets adjacent the mitral valve on the ventricular side.

A first one of the proximal elements cooperates with a first one of the distal elements to form a space for receiving a portion of the anterior leaflet therebetween. A second one of the proximal elements cooperates with a second one of the distal elements to form a space for receiving a portion of the posterior leaflet therebetween. Each such space has an open end and a closed end, and the closed end forms an apex.

The device includes an actuator for selectively moving the distal elements between a first position in which the distal elements are in a collapsed, low profile configuration for delivery of the device, a second position in which the distal elements are in an expanded configuration for positioning the device relative to the mitral valve, and a third position in which the distal elements are secured in position against a portion of the leaflets adjacent the mitral valve on the ventricular side.

The device also includes an actuator for selectively moving the proximal elements between a first position in which the proximal elements are in a collapsed, low profile configuration for delivery of the device and a second position in which the proximal elements are in an expanded configuration for engaging a portion of the leaflets adjacent the mitral valve on the atrial side. Each distal element can also include a distal retaining element positioned along the distal engagement surface. Each distal retaining element is configured to cooperate with a corresponding proximal retaining element to capture a free edge of the mitral valve leaflet as the device is positioned relative to the mitral valve. Each retaining element can be configured to cooperate with a frictional element to allow a leading free edge of the leaflets to move in a first direction toward the body with little or no resistance or restriction and to resist or prevent movement of the free edge of the leaflets in an opposite direction away from the body.

These and other objects and features of the present disclosure will become more fully apparent from the following description and appended claims, or may be learned by the practice of the embodiments of the invention as set forth hereinafter.

BRIEF DESCRIPTION OF THE DRAWINGS

To further clarify the above and other advantages and features of the present disclosure, a more particular description of the invention will be rendered by reference to specific embodiments thereof which are illustrated in the appended drawings. It is appreciated that these drawings depict only illustrated embodiments of the invention and are therefore not to be considered limiting of its scope. Embodiments of the invention will be described and explained with additional specificity and detail through the use of the accompanying drawings in which.

DETAILED DESCRIPTION

I. Introduction

A. Cardiac Physiology

Figure 1:
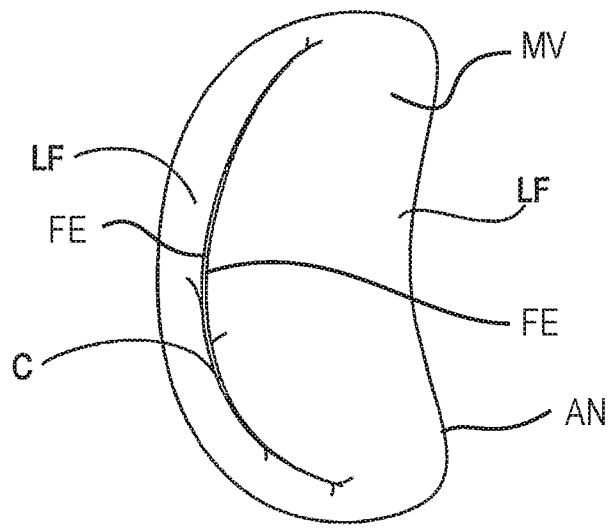
FIG. 1 illustrates free edges of leaflets of the mitral valve in normal coaptation.

As shown in FIG. 1, the mitral valve (MV) comprises a pair of leaflets (LF) having free edges (FE) which, in patients with normal heart structure and function, meet evenly to close along a line of coaptation (C). The leaflets (LF) attach to the surrounding heart structure along an annular region called the annulus (AN). The free edges (FE) of the leaflets (LF) are secured to the lower portions of the left ventricle LV through chordae tendinae (or "chordae").

As the left ventricle of a heart contracts (which is called "systole"), blood flow from the left ventricle to the left atrium through the mitral valve (MV) (called "mitral regurgitation") is usually prevented by the mitral valve.

Figure 2:
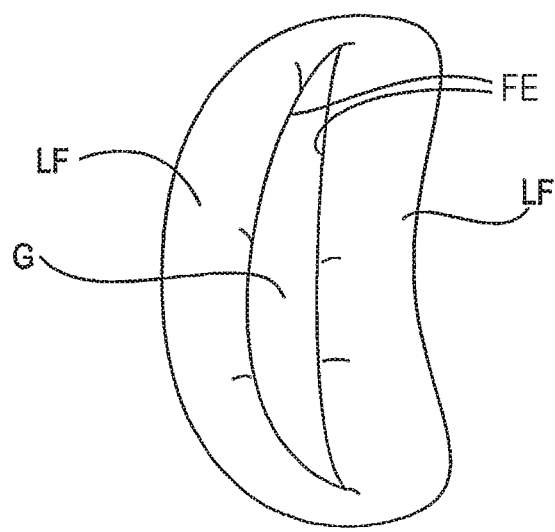
FIG. 2 illustrates the free edges in regurgitative coaptation.

Regurgitation occurs when the valve leaflets do not close properly and allow leakage from the left ventricle into the left atrium. A number of heart structural defects can cause mitral regurgitation. FIG. 2 shows a mitral valve with a defect causing regurgitation through a gap (G).

II. General Overview of Mitral Valve Fixation Technology

Several methods for repairing or replacing a defective mitral valve exist. Some defects in the mitral valve can be treated through intravascular procedures, where interventional tools and devices are introduced and removed from the heart through the blood vessels. One method of repairing certain mitral valve defects includes intravascular delivery of a fixation device to hold portions of the mitral valve tissues in a certain position. One or more interventional catheters may be used to deliver a fixation device to the mitral valve and install it there as an implant to treat mitral regurgitation.

Figure 3A:
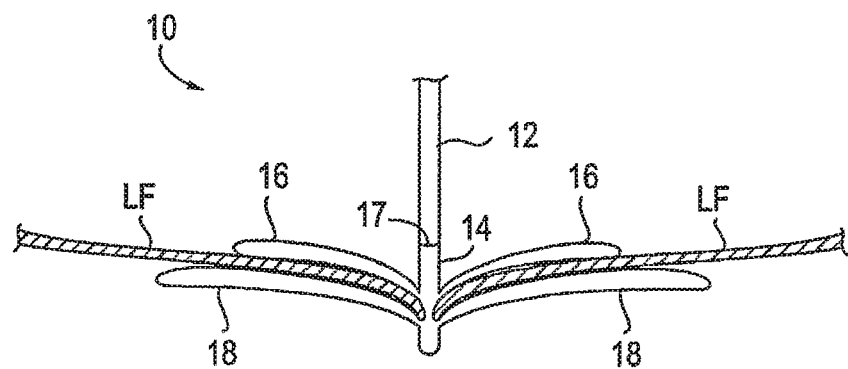
FIGS. 3A-3C illustrate grasping of the leaflets with a fixation device, inversion of the distal elements of the fixation device and removal of the fixation device, respectively.

FIG. 3A illustrates a schematic of an interventional tool 10 with a delivery shaft 12 and a fixation device 14. The tool 10 has approached the mitral valve MV from the atrial side and grasped the leaflets LF.

The fixation device 14 is releasably attached to the shaft 12 of the interventional tool 10 at the distal end of the shaft 12. In this application, when describing devices, "proximal" means the direction toward the end of the device to be manipulated by the user outside the patient's body, and "distal" means the direction toward the working end of the device that is positioned at the treatment site and away from the user. When describing the mitral valve, proximal means the atrial side of the leaflets and distal means the ventricular side of the leaflets.

The fixation device 14 comprises proximal elements 16 and distal elements 18 which protrude radially outward and are positionable on opposite sides of the leaflets LF as shown so as to capture or retain the leaflets therebetween. The fixation device 14 is coupleable to the shaft 12 by a coupling mechanism 17.

Figure 3B:
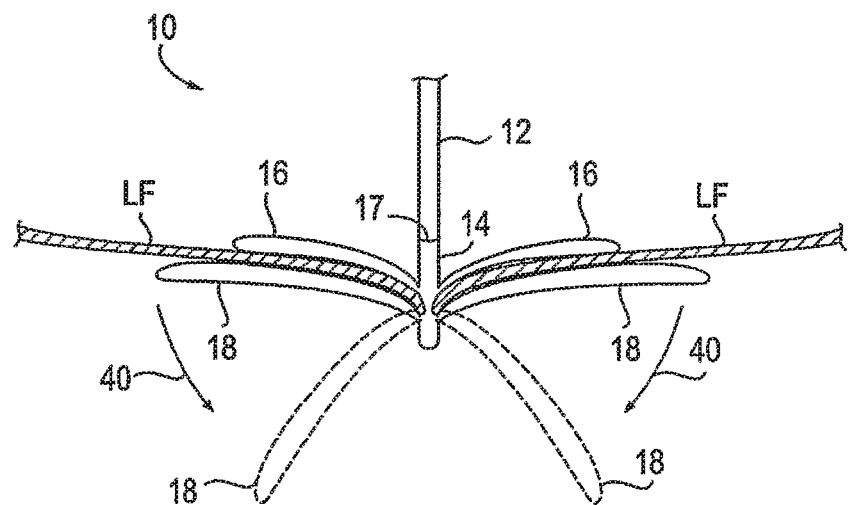
Figure 3C:
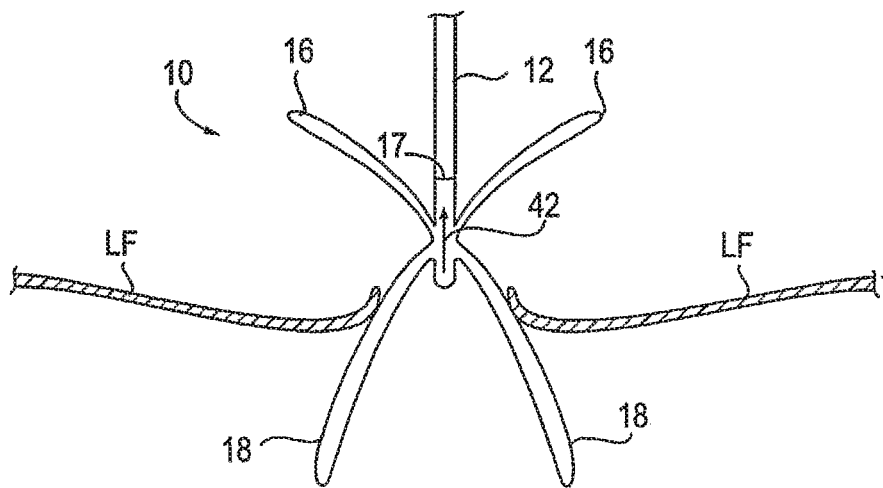

FIG. 3B illustrates that the distal elements 18 may be moved in the direction of arrows 40 to an inverted position. The proximal elements 16 may be raised as shown in FIG. 3C. In the inverted position, the device 14 may be repositioned and then be reverted to a grasping position against the leaflets as in FIG. 3A. Or, the fixation device 14 may be withdrawn (indicated by arrow 42) from the leaflets as shown in FIG. 3C. Such inversion reduces trauma to the leaflets and minimizes any entanglement of the device with surrounding tissues.

Figure 4:
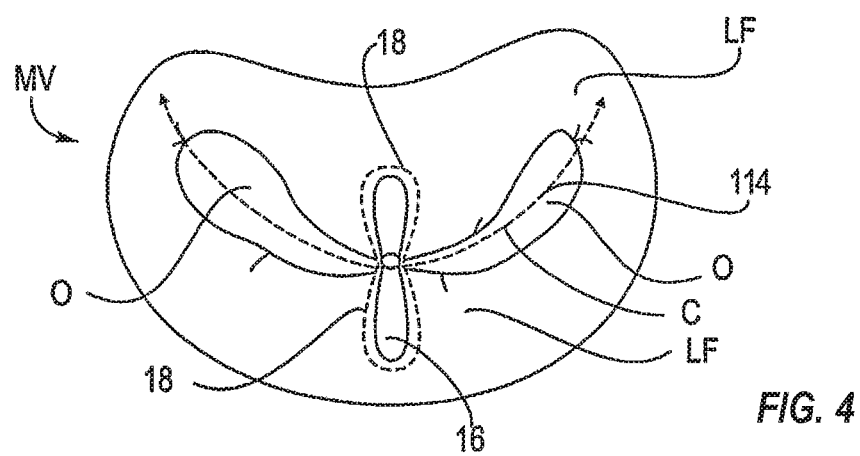
FIG. 4 illustrates the fixation device in a desired orientation relative to the leaflets.

FIG. 4 illustrates the fixation device 14 in a desired orientation in relation to the leaflets LF. The mitral valve MV is viewed from the atrial side, so the proximal elements 16 are shown in solid line and the distal elements 18 are shown in dashed line. The proximal and distal elements 16, 18 are positioned to be substantially perpendicular to the line of coaptation C. During diastole (when blood is flowing from the left atrium to the left ventricle), fixation device 14 holds the leaflets LF in position between the elements 16, 18 surrounded by openings or orifices O which result from the diastolic pressure gradient, as shown in FIG. 4.

Once the leaflets are coapted in the desired arrangement, the fixation device 14 is detached from the shaft 12 and left behind as an implant.

A. Exemplary Fixation Device

Figure 5:
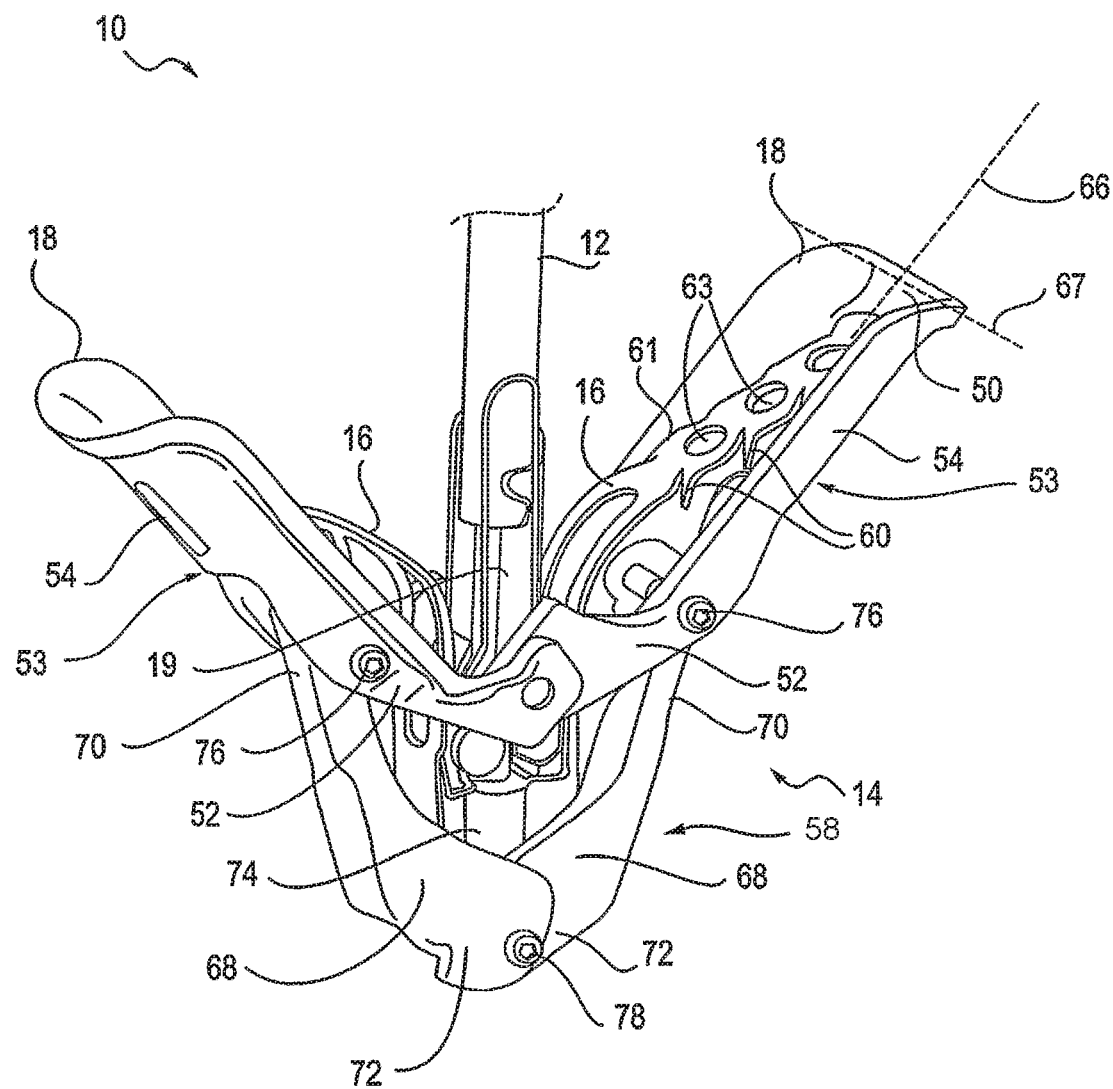
FIG. 5 illustrates an exemplary fixation device coupled to a shaft.

FIG. 5 illustrates an exemplary fixation device 14. The fixation device 14 is shown coupled to a shaft 12 to form an interventional tool 10. The fixation device 14 includes a coupling member 19, a pair of opposed proximal elements 16, and a pair of opposed distal elements 18.

The distal elements 18 comprise elongate arms 53, each arm having a proximal end 52 rotatably connected to the coupling member 19 and a free end 54. Preferably, each free end 54 defines a curvature about two axes, axis 66 perpendicular to longitudinal axis of arms 53, and axis 67 perpendicular to axis 66 or the longitudinal axis of arms 53.

Arms 53 have engagement surfaces 50. Arms 53 and engagement surfaces 50 are configured to engage about 4-10 mm of tissue, and preferably about 6-8 mm along the longitudinal axis of arms 53. Arms 53 further include a plurality of openings.

The proximal elements 16 are preferably resiliently biased toward the distal elements 18. When the fixation device 14 is in the open position, each proximal element 16 is separated from the engagement surface 50 near the proximal end 52 of arm 53 and slopes toward the engagement surface 50 near the free end 54 with the free end of the proximal element 16 contacting engagement surface 50, as illustrated in FIG. 5.

Proximal elements 16 include a plurality of openings 63 and scalloped side edges 61 to increase their grip on tissue. The proximal elements 16 optionally include a frictional element or multiple frictional elements to assist in grasping the leaflets. The frictional elements may comprise barbs 60 having tapering pointed tips extending toward engagement surfaces 50. Any suitable frictional elements may be used, such as prongs, windings, bands, barbs, grooves, channels, bumps, surface roughening, sintering, high-friction pads, coverings, coatings or a combination of these.

The proximal elements 16 may be covered with a fabric or other flexible material. Preferably, when fabrics or coverings are used in combination with barbs or other frictional features, such features will protrude through such fabric or other covering so as to contact any tissue engaged by proximal elements 16.

The fixation device 14 also includes an actuator or actuation mechanism 58. The actuation mechanism 58 comprises two link members or legs 68, each leg 68 having a first end 70 which is rotatably joined with one of the distal elements 18 at a riveted joint 76 and a second end 72 which is rotatably joined with a stud 74. The actuation mechanism 58 comprises two legs 68 which are each movably coupled to a base 69. Or, each leg 68 may be individually attached to the stud 74 by a separate rivet or pin. The stud 74 is joinable with an actuator rod which extends through the shaft 12 and is axially extendable and retractable to move the stud 74 and therefore the legs 68 which rotate the distal elements 18 between closed, open and inverted positions. Immobilization of the stud 74 holds the legs 68 in place and therefore holds the distal elements 18 in a desired position. The stud 74 may also be locked in place by a locking feature. This actuator rod and stud assembly may be considered a first means for selectively moving the distal elements between a first position in which the distal elements are in a collapsed, low profile configuration for delivery of the device, a second position in which the distal elements are in an expanded configuration for positioning the device relative to the mitral valve, and a third position in which the distal elements are secured in position against a portion of the leaflets adjacent the mitral valve on the ventricular side.

Figure 6A:
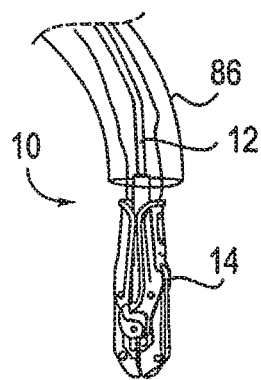
FIGS. 6A-6B, 7A-7B, and 8 illustrate a fixation device in various possible positions during introduction and placement of the device within the body to perform a therapeutic procedure.

FIGS. 6A-6B, 7A-7B, and 8 illustrate various possible positions of the fixation device 14 of FIG. 5. FIG. 6A illustrates an interventional tool 10 delivered through a catheter 86. The catheter 86 may take the form of a guide catheter or sheath. The interventional tool 10 comprises a fixation device 14 coupled to a shaft 12 and the fixation device 14 is shown in the closed position.

Figure 6B:
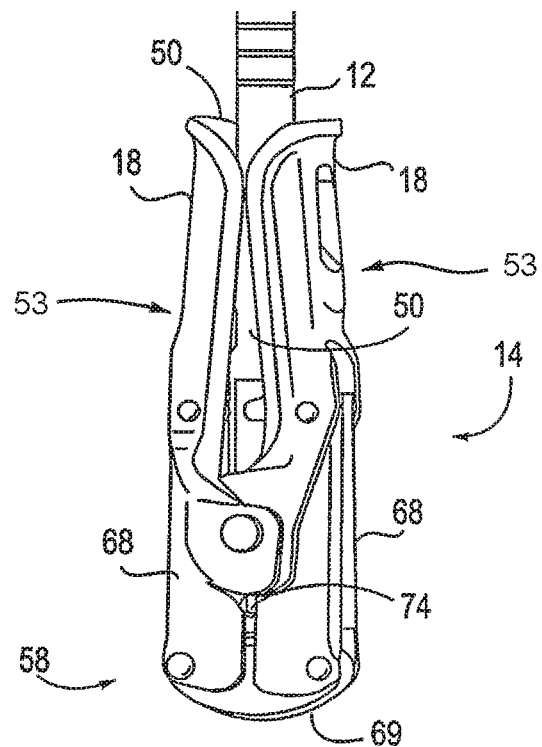

FIG. 6B illustrates a device similar to the device of FIG. 6A in a larger view. In the closed position, the opposed pair of distal elements 18 are positioned so that the engagement surfaces 50 face each other. Each distal element 18 comprises an elongate arm 53 having a cupped or concave shape so that together the arms 53 surround the shaft 12. This provides a low profile for the fixation device 14.

Figure 7A:
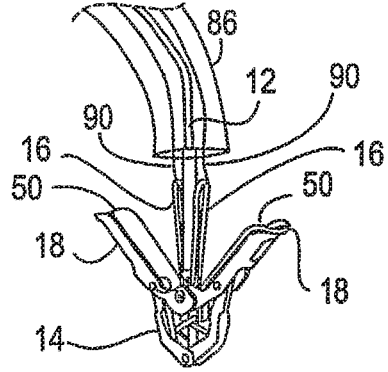
Figure 7B:
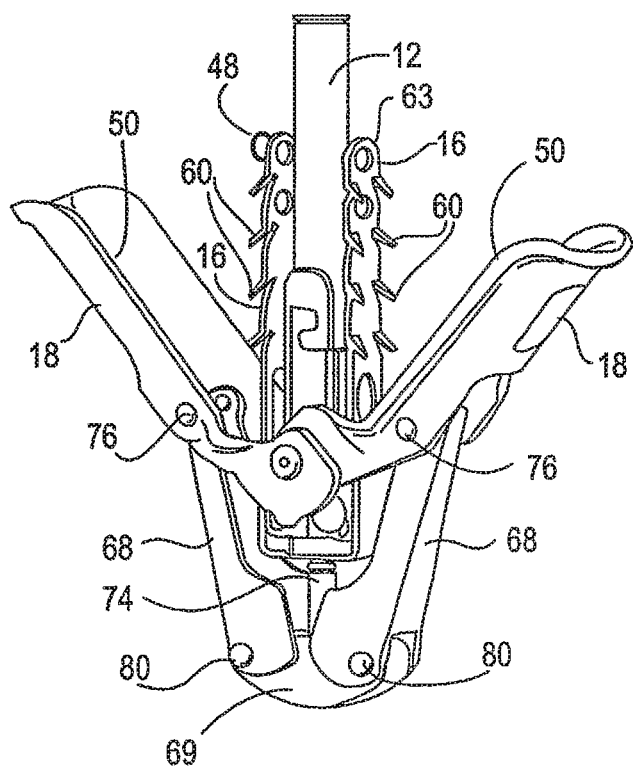

FIGS. 7A-7B illustrate the fixation device 14 in the open position. In the open position, the distal elements 18 are rotated so that the engagement surfaces 50 face a first direction. Distal advancement of the actuator rod relative to shaft 12, and thus distal advancement of the stud 74 relative to coupling member 19, applies force to the distal elements 18 which begin to rotate around joints 76. Such rotation and movement of the distal elements 18 radially outward causes rotation of the legs 68 about joints 80 so that the legs 68 are directed slightly outwards. The stud 74 may be advanced to any desired distance correlating to a desired separation of the distal elements 18. In the open position, engagement surfaces 50 are disposed at an acute angle relative to shaft 12, and are preferably at an angle of between 90 and 180 degrees relative to each other. In the open position, the free ends 54 of arms 53 may have a span therebetween of about 10-20 mm, usually about 12-18 mm, and preferably about 14-16 mm.

Proximal elements 16 are typically biased outwardly toward arms 53. The proximal elements 16 may be moved inwardly toward the shaft 12 and held against the shaft 12 with the aid of proximal element lines 90 which can be in the form of sutures, wires, nitinol wire, rods, cables, polymeric lines, or other suitable structures. The proximal element lines 90 extend through the shaft 302 of the delivery catheter 300 and connect with the proximal elements 16. The proximal elements 16 are raised and lowered by manipulation of the proximal element lines 90. Once the device is properly positioned and deployed, the proximal element lines can be removed by withdrawing them through the catheter and out the proximal end of the device 10. The proximal element lines 90 may be considered a second means for selectively moving the proximal elements between a first position in which the proximal elements are in a collapsed, low profile configuration for delivery of the device and a second position in which the proximal elements are in an expanded configuration for engaging a portion of the leaflets adjacent the mitral valve on the atrial side.

In the open position, the fixation device 14 can engage the tissue which is to be approximated or treated. The interventional tool 10 is advanced through the mitral valve from the left atrium to the left ventricle. The distal elements 18 are then deployed by advancing actuator rod relative to shaft 12 to thereby reorient distal elements 18 to be perpendicular to the line of coaptation. The entire assembly is then withdrawn proximally and positioned so that the engagement surfaces 50 contact the ventricular surface of the valve leaflets, thereby engaging the left ventricle side surfaces of the leaflets. The proximal elements 16 remain on the atrial side of the valve leaflets so that the leaflets lie between the proximal and distal elements. The interventional tool 10 may be repeatedly manipulated to reposition the fixation device 14 so that the leaflets are properly contacted or grasped at a desired location. Repositioning is achieved with the fixation device in the open position. In some instances, regurgitation may also be checked while the device 14 is in the open position. If regurgitation is not satisfactorily reduced, the device may be repositioned and regurgitation checked again until the desired results are achieved.

Figure 8:
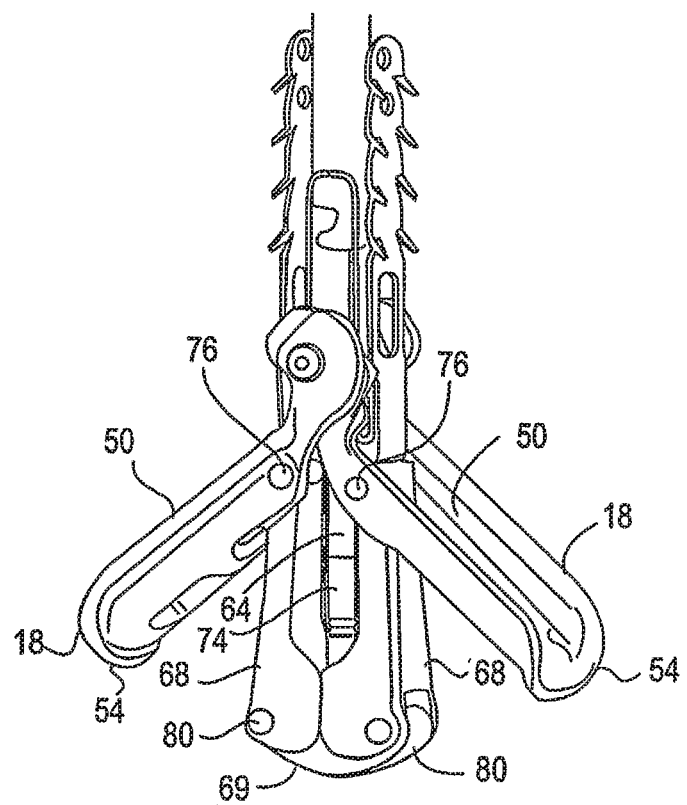

It may also be desired to invert distal elements 18 of the fixation device 14 to aid in repositioning or removal of the fixation device 14. FIG. 8 illustrates the fixation device 14 in the inverted position. By further advancement of actuator rod relative to shaft 12, and thus stud 74 relative to coupling member 19, the distal elements 18 are further rotated so that the engagement surfaces 50 face outwardly and free ends 54 point distally, with each arm 53 forming an obtuse angle relative to shaft 12.

The angle between arms 53 when the device is inverted is preferably in the range of about 270 to 360 degrees. Further advancement of the stud 74 further rotates the distal elements 18 around joints 76. This rotation and movement of the distal elements 18 radially outward causes rotation of the legs 68 about joints 80 so that the legs 68 are returned toward their initial position, generally parallel to each other. The stud 74 may be advanced to any desired distance correlating to a desired inversion of the distal elements 18. Preferably, in the fully inverted position, the span between free ends 54 is no more than about 20 mm, usually less than about 16 mm, and preferably about 12-14 mm. Barbs 60 are angled slightly in the distal direction (away from the free ends of the proximal elements 16), reducing the risk that the barbs will catch on or lacerate tissue as the fixation device is withdrawn.

Once the distal elements 18 of the fixation device 14 have been positioned in a desired location against the left ventricle side surfaces of the valve leaflets, the leaflets may then be captured between the proximal elements 16 and the distal elements 18. The proximal elements 16 are lowered toward the engagement surfaces 50 by releasing tension from proximal element lines 90, thereby releasing proximal elements 16 so that they are then free to move, in response to the internal spring bias force formed into proximal elements 16, from a constrained, collapsed position to an expanded, deployed position and so that the leaflets are held between the proximal elements 16 and the distal elements 18. If regurgitation is not sufficiently reduced, the proximal elements 16 may be raised and the distal elements 18 adjusted or inverted to reposition the fixation device 14.

After the leaflets have been captured between the proximal and distal elements 16, 18 in a desired arrangement, the distal elements 18 may be locked to hold the leaflets LF in this position or the fixation device 14 may be returned to or toward a closed position. This is achieved by retraction of the stud 74 proximally relative to coupling member 19 so that the legs 68 of the actuation mechanism 58 apply an upwards force to the distal elements 18 which in turn rotate the distal elements 18 so that the engagement surfaces 50 again face one another. The released proximal elements 16 which are biased outwardly toward distal elements 18 are concurrently urged inwardly by the distal elements 18. The fixation device 14 may then be locked to hold the leaflets in this closed position. The fixation device 14 may then be released from the shaft 12. The fixation device 14 optionally includes a locking mechanism for locking the device 14 in a particular position, such as an open, closed or inverted position or any position therebetween. The locking mechanism may include a release harness. Applying tension to the release harness may unlock the locking mechanism.

The lock lines 92 engage the release harnesses 108 of the locking mechanism 106 to lock and unlock the locking mechanism 106. The lock lines 92 extend through the shaft 302 of the delivery catheter 300. A handle attached to the proximal end of the shaft is used to manipulate and decouple the fixation device 14.

Additional disclosure regarding such fixation devices 14 may be found in PCT Publication No. WO 2004/103162 and U.S. patent application Ser. No. 14/216,787, the disclosures of both of which are incorporated herein in their entirety.

B. Improved Grasping Mechanisms

Sometimes it can be difficult to capture or retain tissue within fixation device 14 so that fixation device 14 approximates or repairs the tissue as desired. Leaflet insertion may be assessed throughout the process of installing a fixation device 14, but it can be difficult to differentiate good and poor leaflet insertion and retention. For example, when fixation device 14 is used in endovascular or minimally invasive procedures, visualization of the capturing or retention of tissue may be difficult.

At times during the process of installing a fixation device 14, the tissue desired to be captured or retained between proximal elements 16 and distal elements 18 may seem to be securely captured or retained when it is actually only partially captured or insecurely captured. As a result, the free edges FE of leaflet tissue LF may later disassociate from the fixation device 14 and the fixation device 14 may then not properly coapt, approximate, or repair the tissue. Even if imaging methods make it possible to visualize when tissue is captured in the fixation device, they may not allow for a viewer to distinguish between securely and insecurely captured tissue. For example, color Doppler echo may show that regurgitation has been reduced, but it may not provide precise specifics on where along the leaflets LF fixation device 14 has captured the tissue, and whether the capturing is secure.

If a leaflet is poorly grasped between proximal elements 16 and distal elements 18, eventually that leaflet LF may separate from the fixation device 14. This may result in the fixation device 14 being attached to only one of the leaflets LF, or separating from both leaflets LF, and no longer functioning as desired.

In addition to difficulties arising from the imaging or visualization of the device 14 as it is installed, difficulty in capturing or retaining tissue within fixation device 14 may also result from the nature of tissue desired to be captured or retained. For example, when using fixation device 14 to fix mitral valve leaflets LF to each other to stop or reduce mitral valve regurgitation, the leaflets LF are constantly moving as the heart beats.

FIGS. 9-12 illustrate various embodiments that are intended to help a fixation device 14' capture and retain the free edges FE of leaflets LF during placement of the fixation device 14'. To do so, these embodiments include the addition of a retaining element 400 positioned on the proximal side of each distal element 18'. The retaining element 400 combines with frictional elements such as barbs 410 at the lower end of the proximal element 16' to capture the free edge FE of the leaflet upon its initial insertion and help retain it there until the proximal and distal elements are fully deployed. The lower end of the proximal element 16' is the end closest to the stud 74'.

The retaining element 400 and barbs 410 are configured to cooperate to allow the free edge FE of the leaflets LF to easily or freely move in a first direction toward the apex 430 formed between each proximal element 16' and the corresponding distal element 18', but at the same time to resist or prevent movement of the free edge FE of the leaflet tissue LF in the opposite direction away from apex 430. In this way, retaining element 400, in cooperation with the barbs 410, help to retain the leaflets LF in the device 14' while the device is being positioned relative to the leaflets LF and before the proximal elements 16' and distal elements 18' are fully deployed.

The retaining element 400 may serve as a passive capture mechanism that retains leaflet tissue LF without needing to be activated. For example, the retaining element 400 may retain leaflet tissue LF in the device 14' when a length of tissue of about 4-10 mm, and preferably about 6-8 mm, is located along the longitudinal axis of the distal elements 18'. A retaining element 400 may be located on the distal elements 18', as shown in the illustrated embodiments, or the retaining element 400 may be located on the proximal elements 16', or it may be located on both the distal elements 18' and the proximal elements 16'. A retaining element 400 may hold a leaflet LF in place without closing the fixation element 18' and gripping element 16'.

Figure 9A:
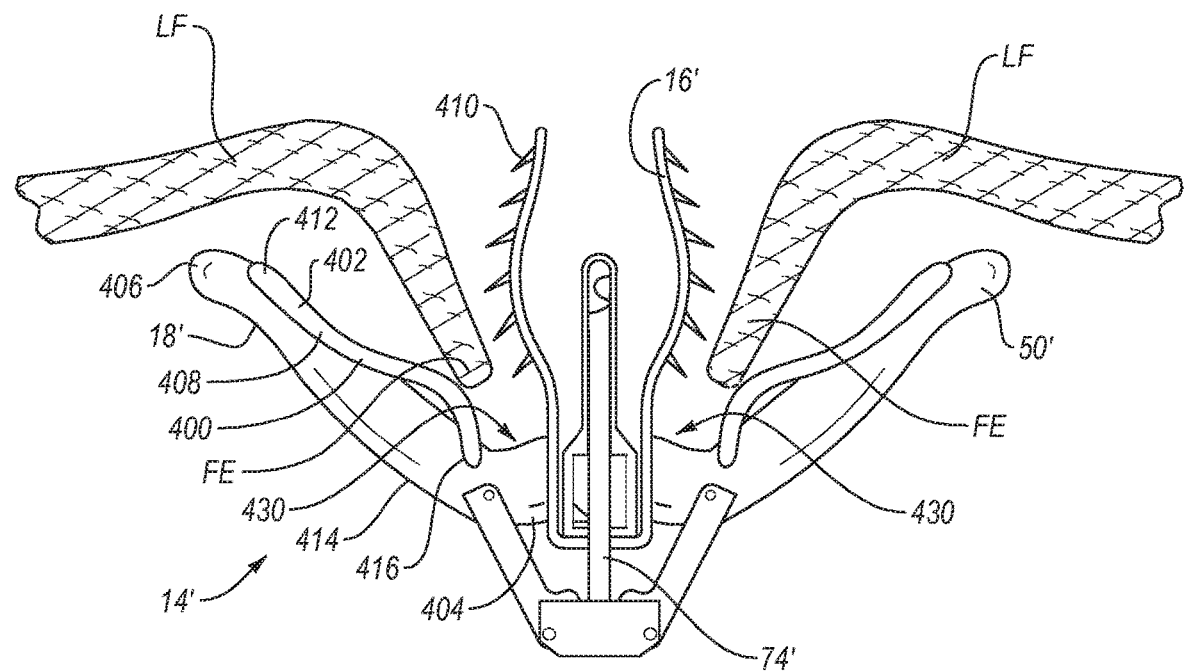
FIGS. 9A-9B illustrate a fixation device embodiment with a leaf spring.
Figure 9B:
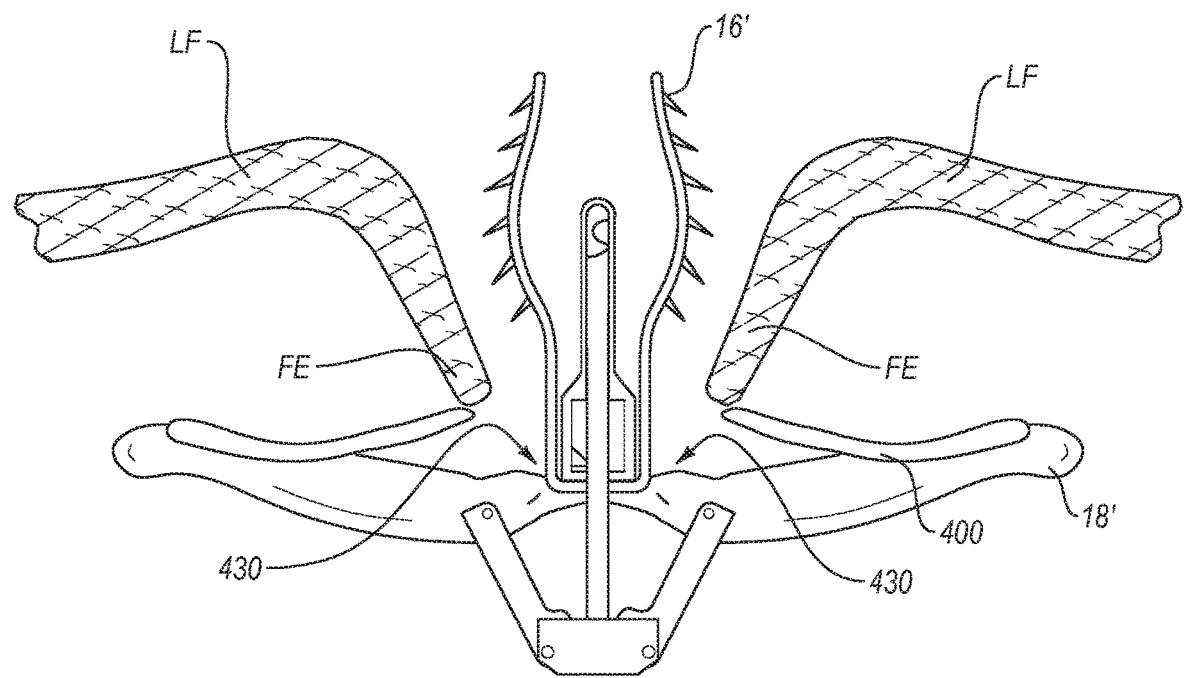

As shown in FIGS. 9A-9B, in one embodiment, a retaining element 400 may be a spring element 402 that retains leaflets LF inserted into the fixation device 14'. The spring element 402 may help capture or hold any leaflet LF that inserts past a given point along the distal elements 18' which is determined to be sufficient insertion depth.

Referring again to FIGS. 9A-B, the spring element 402 is on a distal element 18'. Each distal element 18' has a spring element 402 incorporated into or attached to the distal element 18'. The spring element 402 may be incorporated into or attached to the distal element 18' at a midpoint 414 between a first end 404 of the distal element 18' that attaches to a stud 74' and the free end 406 of the distal element 18'. It may also be incorporated into or attached to the distal element 18' closer to the free end 406 of each distal element 18' or to the first end 404 of each distal element 18'. As shown in FIGS. 9A-B, the fixed end 412 of the spring element 402 is located between the midpoint 414 and free end 406 of the distal element 18'. In addition, the spring element 402 of the retaining element 400 is elongate and can extend in an elongate fashion along substantially an entire length of the distal element 18' and associated distal engagement surface. Alternatively, the retaining element 400 can extend in an elongate fashion from a location near or adjacent first end 404 to a location distal a midpoint of the distal engagement surface of the distal element 18' or from a location near or adjacent second end 406 to a location distal a midpoint of the distal engagement surface of the distal element 18'.

The spring element 402 may comprise a low-force leaf spring 408 biased to push the spring element 402 towards the leaflet LF and encourage frictional elements or barbs 410 to be deeply inserted into the leaflet LF, so the leaflet LF remains in a fully seated state until distal elements 18' are further closed. As illustrated, barbs 410 are orientated at an angle pointing toward apex 430. With barbs 410 oriented in that direction, the leading edge LE of the leaflet tissue LF is allowed to move in a first direction toward apex 430 with little or no restriction or resistance. As the leading edge LE of the leaflet tissue moves toward apex 430, spring element 402 directs or urges the leaflet tissue LF toward and into contact with barbs 410. Once the leaflet tissue LF comes into contact with and engages the barbs 410, the angled orientation of the barbs 410 causes barbs 410 to penetrate into the leaflet tissue LF and then restricts or prevents movement of the leaflet tissue LF in the opposite direction away from apex 430. Thus, the combination of the retaining element 400 and the barbs 410 effectively function as a directional trap that permits the leaflet tissue LF to move in a first direction toward apex 430 with little or no resistance, while restricting or preventing movement of the leaflet tissue LF in a second or opposite direction away from apex 430.

The leaf spring 408 may have one or more lobes or a partial lobe. The leaf spring 408 may be biased to allow for little to no resistance to a leaflet LF as it inserts. It may have surface features, a pointed edge, or other elements that create resistance to make it difficult for the leaflet LF to retract out. Such surface features may include, for example, dimples, bumps, ridges, or indents. For example, as shown in FIG. 9A-B, the free end 416 of the spring element 402 may be configured to curve toward the distal elements 18' (as shown in FIG. 9A) when tissue LF is being trapped, and curve away from the distal element 18' (as shown in FIG. 9B) when tissue LF is being released. When the leaflet is entrapped between the distal elements 18' and the proximal elements 16', the free end 416 of the spring element 402 may be configured to lie flat against the distal element 18'.

The retaining element 400 helps the fixation device 14 capture tissue when proximal elements 16' are raised and distal elements 18' are still partially open. The retaining element 400 may be configured to urge the leaflet tissue against the barbs 410 on the proximal elements 16. The retaining element 400 may be a one-way mechanism that allows tissue to enter but not exit, such as a ratchet or something similar to a ratchet.

Because repositioning and regrasping the fixation device 14' is sometimes required, the one-way mechanism should have a way for the leaflet tissue LF to be permitted to escape. The retaining element can be designed to allow tissue to exit under certain circumstances, such as when the distal elements 18' are opened to approximately 180°, as shown in FIG. 9B, or are opened even further in an inverted position, as shown in FIG. 8. Or, when the proximal elements 16' are raised, the leaflet tissue LF may be released to allow regrasping.

To ensure that the leaflets LF are properly grasped in a fixation device 14', one method of using a device with a retaining element 400 such as a spring element 402 located near each set of distal elements 18' and proximal elements 16' is to first capture one or both leaflets LF in the spring element 402. The spring element urges the leaflets LF against the barbs 410 at the lower end of the proximal element 16' to capture the free edge FE of the leaflet LF upon its initial insertion and help retain it there until the proximal and distal elements 16, 18 are fully deployed.

It may be possible to confirm that one or more leaflets LF is captured based on imaging methods such as color Doppler echo. When leaflets LF are trapped between the spring element 402 and the barbs 410, then the proximal elements 16' may be lowered toward the surfaces 50' of the distal elements 18', so that the leaflets LF are held therebetween and the distal elements 18' may be locked to hold the leaflets LF in this position or the fixation device 14' may be returned to or toward a closed position.

Figure 10:
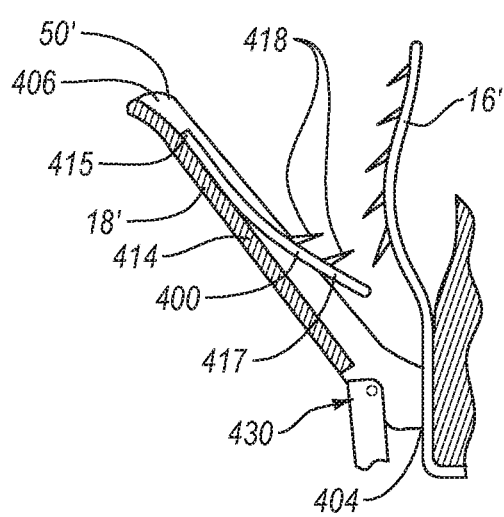
FIG. 10 illustrates a close-up of a portion of another embodiment of a fixation device.
Figure 11A:
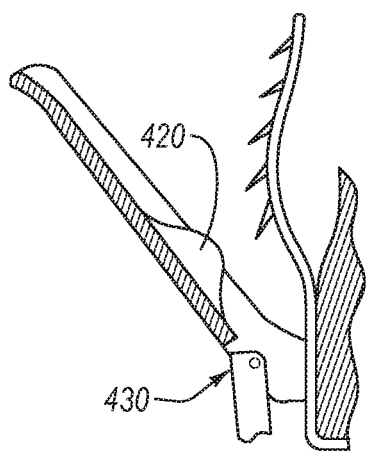
FIG. 11A illustrates a close-up of a portion of another embodiment of a fixation device.
Figures 11B, 11C:
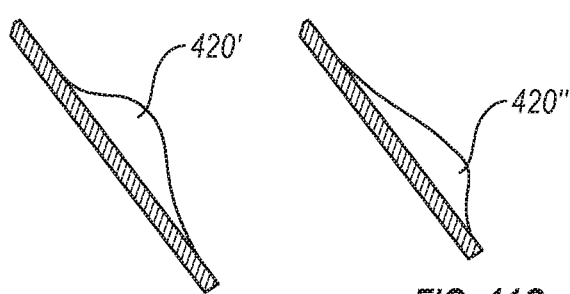
FIGS. 11B and 11C each illustrate a close-up cross-sectional side view of a portion of another embodiment of a fixation device.
Figure 11D:
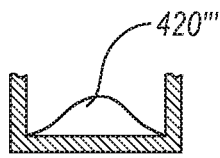
FIGS. 11D and 11E each illustrate a close-up cross-sectional transverse view of a portion of another embodiment of a fixation device.
Figure 11E:
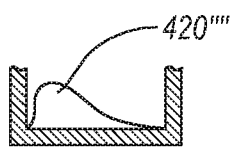

In another embodiment, as shown in FIG. 10, a retaining element 400 comprises an arm 417. Each distal element 18' has an arm 417 incorporated into or attached to the distal element 18'. The arm 417 may be incorporated into or attached at a fixed end 415 to the distal element 18' at a midpoint 414 between a first end 404 of the distal element 18' that attaches to a stud 74' and the free end 406 of the distal element 18'. It may also be incorporated into or attached to the distal element 18' closer to the free end 406 of each distal element 18' or to the first end 404 of each distal element 18'. As shown in FIG. 10, the fixed end 415 of the arm 417 is located between the midpoint 414 and free end 406 of the distal element 18'.

The arm 417 has a projection or projections 418 of a suitable shape and size to assist in retaining the leaflets LF in position. These projections 418 may have sharp tips located opposite to the arm 417, or sharp edges between their tips and the arm 417. They may comprise barbs having tapering pointed tips, scalloped edges, prongs, windings, bands, grooves, channels, bumps, surface roughening, sintering, high-friction pads, coverings, coatings or a combination of these. As shown in FIG. 10, these projections may be oriented away from the surface 50' and angled away from the free ends 406 of the distal element 18'. They may also orient toward the free ends 406, or be perpendicular to the surface 50'. The projections may flex or collapse toward the distal element 18' when the fixation device 14' is closed and flex out to a fixed angle when the fixation device 14' is open. For example, the projections 418 may bias toward a fixed angle from the engagement surfaces 50', but may be pushed flat against the distal element 18' when the distal elements 18' close around the shaft 12.

The fixation device should be configured with enough space between the proximal elements 16' and the distal elements 18' for a leaflet LF to be easily inserted past the projections 418 on the distal elements 18'. The chordal tethered leaflets LF may be tensioned lightly upon the fixation device 14' just prior to closing the distal elements 18' and proximal elements 16'. They may also be securely affixed to the device 14' prior to closing the distal elements 18' and proximal elements 16'.

In one embodiment, the arm 417 may be a flexible leaf-spring that pivots at a fixed end 415 and is positioned between the proximal element 16' and distal elements 18'. It may also include a system of projections 418 angled to allow entry of the tissue between the distal element 18' and proximal element 16', but to prevent retraction of the tissue LF. As shown, the projection 418 and leaf spring 417 may be combined in the same structure. In addition, the arm 417 of the retaining element 400 is elongate and can extend in an elongate fashion along substantially an entire length of the distal element 18' and associated distal engagement surface. Alternatively, the retaining element 400 can extend in an elongate fashion from a location near or adjacent first end 404 to a location distal a midpoint of the distal engagement surface of the distal element 18' or from a location near or adjacent second end 406 to a location distal a midpoint of the distal engagement surface of the distal element 18'.

As shown in FIG. 11, in another embodiment the retaining element 400 may comprise one or more protrusions 420. One or more protrusions 420 may be positioned close to the hinge point of the distal elements 18' on the engagement surface 50'. When a leaflet LF is inserted past the protrusion 420, the protrusion 420 may reduce leaflet detachment upon deployment of the fixation device 14' by directing or urging the leaflet LF into contact with the gripping surfaces or barbs 410 located on the opposing proximal element 16'. The protruding feature 420 may be located near a midpoint 414 between a first end 404 of the distal element 18' that attaches to a stud 74' and the free end 406 of the distal element 18'. It may also be incorporated into or attached to the distal element 18' closer to the free end 406 of each distal element 18' or to the first end 404 of each distal element 18'. A protruding feature 420 may be a rigid piece of material that is affixed to the engagement surface 50' of distal elements 18' and may be atraumatic to aid with directing or urging the leaflet LF while causing minimal damage to the leaflet LF, such as not penetrating or puncturing the leaflet LF. The protruding feature may be comprised of any biocompatible material or materials, such as a polymer, nitinol, or other alloys, or bioabsorbable materials.

The protruding feature 420 of the distal elements 18' may passively engage the leaflet tissue LF when leaflet tissue LF is sufficiently inserted into the device 14'. Or, the protruding feature 420 may be configured to help engage leaflet tissue and secure it into position when the proximal elements 16' are lowered and also secure the leaflet tissue LF. The protruding feature 420 may help entrap tissue between the protruding feature 420 and the gripping surfaces of the proximal elements 16'. The feature 420 may urge the tissue LF against the barbs 410.

While the protruding feature 420 is illustrated as including a generally curved or domed outer surface, it will be understood that various other surface orientations are appropriate while maintaining the atraumatic nature and ability to aid with directing or urging the leaflet LF. For instance, as illustrated in FIGS. 11B-11E, the protruding feature 420 can have a curved surface that is symmetric or asymmetric in (i) a direction from first end 404 towards the second end 406. (ii) a direction cross-wise, transverse, or oblique to the direction from first end 404 towards the second end 406, or (iii) both. So the protruding feature 420 can be symmetric in at least one axis, at least two axes, or in all three axes. Alternatively, the protruding feature 420 can be asymmetric in at least one axis, at least two axes, or in all three axes.

Figure 12:
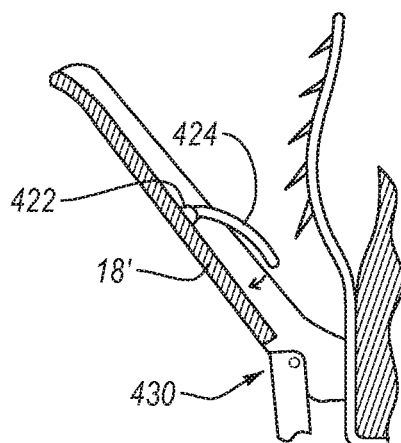
FIG. 12 illustrates a close-up of a portion of another embodiment of a fixation device.

In another embodiment, shown in FIG. 12, the retaining element 400 may comprise a hinge 422 that is attached to the surface 50' of the distal elements 18'. The hinge 422 connects to an arm 424 that can swing toward and away from the distal element 18'. As shown in FIG. 12, the arm 424 may bias toward the first end 404 of each distal element 18'. The arm 424 may be capable of laying parallel to or flat against the surface 50' while being oriented toward the first end 404 of the distal element 18'. It also may be capable of laying parallel to or flat against the surface 50' while being oriented toward the free end 406 of the distal element 18', and therefore capable of rotating 180°. The hinge 422 may restrict the movement of the arm 424 so that it can, for example, only lie parallel to the surface 50' while being oriented toward the first end 404 of the distal element 18' and be rotated about 90°, so that the angle formed between the arm 424 and the portion of the distal element 18' below the hinge 422 can be no greater than 90°. The hinge 422 may also be a pivoting element.

There may also be multiple arms 424 on the distal element 18'. For example, there may be two arms, each located the same distance between the ends 404 and 406, and positioned next to each other on the engagement surface 50'. If there are multiple retaining elements 400, such as multiple arms 424 or multiple spring elements 402, they may be configured to be positioned on either side of the barbs 410 on the proximal element. Retaining element or elements 400 may also be positioned to be located between barbs 410 on the proximal element 16', if there are multiple barbs 410 on the proximal element 16'. In addition, the arm 424 of the retaining element 400 is elongate and can extend in an elongate fashion along substantially an entire length of the distal element 18' and associated distal engagement surface. Alternatively, the retaining element 400, and associated arm 424, can extend in an elongate fashion from a location near or adjacent first end 404 to a location distal a midpoint of the distal engagement surface of the distal element 18' or from a location near or adjacent second end 406 to a location distal a midpoint of the distal engagement surface of the distal element 18'.

The distal elements 18 may be covered with a fabric or other flexible material. Preferably, when fabrics or coverings are used in combination with projections 418, such features will protrude through such fabric or other covering so as to contact the leaflet tissue LF.

Analogous to a mechanical pawl, the bias, angle, and direction of a retaining element 400 may allow the leaflet to fall or slide deeper towards the stud 74' without much resistance but may restrict the ability of the leaflet LF to move back out. By permitting the leaflet LF to easily enter but not permitting it to easily be removed from the fixation device 14', this may help entrap the leaflet LF in a fully inserted state.

In the embodiments described above, the retaining element 400 is a passive element. However, retaining element 400 may also include an active element such that, when a piece of leaflet tissue LF proceeds beyond or next to a portion of the retaining element 400, the retaining element 400 may automatically spring or deploy in such a way as to retain tissue LF in place.

In another embodiment, a fixation device 14 or 14' may comprise a mechanical or physical sensor or some visual indicator of when a leaflet is properly inserted into the device prior to closing the distal elements 18' and deployment of the fixation device 14 or 14'. For example, a tactile sensor may be embedded near the first end 404 of each distal element. Each tactile sensor may provide a signal or indication when the leaflet LF touches the sensor, and the sensor may be located so that the leaflet LF will be unable or unlikely to touch the sensor unless the leaflet is adequately captured.

Yet another mechanism for enhancing the placement and retention of the leaflet tissue LF in the fixation device 14 or 14' is to facilitate actuation of each proximal element 16 or 16' and each distal element 18 or 18' independent from one another. When the proximal elements 16 or 16' for both leaflets LF are activated simultaneously, and the distal elements 18 or 18' for each leaflet LF are also activated simultaneously, it can be hard to capture both leaflets, because it is necessary to capture both at the same time. In other words, when the activation of both proximal elements 16 or 16' is symmetric, and the activation of both distal elements 18 or 18' is symmetric, the fixation device 14 or 14' is not able to grasp one leaflet first and then the other. If a catheter or the fixation device 14 or 14' is not properly positioned, or if either leaflet LF has redundant or loose length, the fixation device 14 or 14' may not fully seat the leaflets between each distal fixation element 18 or 18' and proximal gripping element 16 or 16'.

In one embodiment, each proximal element 16 or 16' and/or each distal element 18 or 18' may be activated independently from each other. For example, there may be a separate proximal element line for each proximal element 16 or 16'. Similarly, there may be two actuator rods 64 which extend through the shaft 12, each of which may be configured to activate one distal element 18 or 18'.

In addition to being used to repair mitral valves, these devices can be used in a variety of therapeutic procedures, including endovascular, minimally-invasive, and open surgical procedures, and can be used in various anatomical regions, including abdominal, thoracic, cardiovascular, intestinal, digestive, respiratory, and urinary systems, and other systems and tissues. The invention provides devices, systems, and methods that may more successfully approximate and repair tissue by improving the capture of tissue into the devices.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A fixation implant for fixation of leaflets of a heart valve comprising:
   first and second distal elements moveable between an open position and a closed position, each distal element extending outwardly from a center of the fixation implant in the open position;
   the first retaining element extending from the first distal element toward the center of the fixation implant in the open position, wherein the first retaining element is pivotally coupled to the first distal element, the first retaining element angled relative to the first distal element in the open position and parallel to the first distal element in the closed position;
   the second retaining element extending from the second distal element toward the center of the fixation implant in the open position, wherein the second retaining element is pivotally coupled to the second distal element, the second retaining element angled relative to the second distal element in the open position and parallel to the second distal element in the closed position;

a first proximal element movable to capture a first leaflet of the heart valve between the first proximal element and the first retaining element; and a second proximal element moveable to capture second leaflet of the heart valve between the second proximal element and the second retaining element, wherein the first and second distal elements are configured to cover the first and second retaining elements, respectively, in the closed position.

2. The fixation implant of claim 1, wherein the first retaining element extends at least to a location distal a midpoint of the first distal element, and the second retaining element extends at least to a location distal a midpoint of the second distal element.

3. The fixation implant of claim 1, wherein the first retaining element is configured to pivot up to 180 degrees relative to the first distal element and the second retaining element is configured to pivot up to 180 degrees relative to the second distal element.

4. The fixation implant of claim 1, wherein each proximal element includes a plurality of friction elements.

5. The fixation implant of claim 4, wherein the plurality of friction elements comprises a plurality of barbs.

6. The fixation implant of claim 4, wherein each of the first and second retaining elements is configured to cooperate with the plurality of friction elements of the respective proximal element to allow a leading free edge of the first leaflet of the heart valve and the second leaflet of the heart valve, respectively, to move freely in a first direction toward the center of the fixation implant and to restrict movement of the leading free edge of the respective first and second leaflet of the heart valve in a second direction opposite the first direction.

7. The fixation implant of claim 1, further comprising at least two sutures configured to raise and lower each of the first and second proximal elements relative the first and second retaining elements, respectively.

8. The fixation implant of claim 1, wherein each of the first and second distal elements includes a fabric covering.

9. The fixation implant of claim 8, wherein each of the first and second distal elements has a concave surface.

10. The fixation implant of claim 9, wherein the concave surfaces of the first and second distal elements are configured to surround a central portion of the fixation implant in the closed position.

11. The fixation implant of claim 10, wherein the central portion has a longitudinal axis defining the center of the fixation implant.

12. The fixation implant of claim 1, wherein each of the first and second distal elements has an outwardly extending end in the open position, and wherein each of the first and second retaining elements is attached to the respective first and second distal element near the corresponding outwardly extending end.

13. The fixation implant of claim 1, further comprising a hinge between each of the first and second retaining elements and the respective first and second distal element.

14. The fixation implant of claim 13, wherein each of the first and second retaining element can swing toward and away from the respective first and second distal element about the corresponding hinge.

15. The fixation implant of claim 13, wherein each of the first and second retaining elements is capable of rotating 180 degrees about the corresponding hinge.

* * * * *